United States Patent
Bjurbo et al.

(10) Patent No.: US 12,128,194 B2
(45) Date of Patent: *Oct. 29, 2024

(54) SYSTEM AND METHOD FOR DETECTING MEDICAL DEVICE LOCATION AND ORIENTATION IN RELATION TO PATIENT ANATOMY

(71) Applicant: Avent, Inc., Alpharetta, GA (US)

(72) Inventors: Karl Thomas Bjurbo, Cumming, GA (US); Anthony D. Roberts, Canton, GA (US); Shawn G. Purnell, Sandy Springs, GA (US); Vlad Bluvshtein, Plymouth, MN (US)

(73) Assignee: Avent, Inc., Alpharetta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/347,700

(22) Filed: Jul. 6, 2023

(65) Prior Publication Data
US 2023/0338708 A1   Oct. 26, 2023

Related U.S. Application Data

(63) Continuation of application No. 17/007,576, filed on Aug. 31, 2020, now Pat. No. 11,730,926.

(51) Int. Cl.
*A61M 25/01* (2006.01)
*A61B 34/00* (2016.01)
(Continued)

(52) U.S. Cl.
CPC ......... *A61M 25/0127* (2013.01); *A61B 34/25* (2016.02); *A61M 25/0102* (2013.01);
(Continued)

(58) Field of Classification Search
None
See application file for complete search history.

(56) References Cited

U.S. PATENT DOCUMENTS

| | | | |
|---|---|---|---|
| 5,646,525 | A | 7/1997 | Gilboa |
| 5,755,725 | A | 5/1998 | Druais |

(Continued)

FOREIGN PATENT DOCUMENTS

| | | | |
|---|---|---|---|
| EP | 3 284 402 A1 | 2/2018 | |
| EP | 3 639 734 A1 | 4/2020 | |

*Primary Examiner* — Saptarshi Mazumder
(74) *Attorney, Agent, or Firm* — Meunier Carlin & Curfman LLC

(57) ABSTRACT

A medical device position guidance system is provided. The system includes at least one reference transmitter and a receiver system configured to receive signals from the at least one reference transmitter. The reference transmitter is configured to maintain a static position on a subject. The system further includes a processor configured to (i) receive signals relating to the location and orientation of each sensor of the receiver system relative to the at least one reference transmitter; and (ii) using the received signals, create an anatomical coordinate system. The system may further include an inserted transmitter configured to be attached to a medical device. The inserted transmitter is adapted to establish the location and orientation of the medical device within the anatomical coordinate system. A method for medical device position guidance is also provided.

13 Claims, 13 Drawing Sheets

(51) Int. Cl.
*A61B 34/10* (2016.01)
*A61B 34/20* (2016.01)

(52) U.S. Cl.
CPC ... *A61M 25/0108* (2013.01); *A61B 2034/105* (2016.02); *A61B 2034/2051* (2016.02); *A61B 2034/2063* (2016.02); *A61B 2034/2072* (2016.02); *A61M 2025/0166* (2013.01)

(56) References Cited

U.S. PATENT DOCUMENTS

| | | |
|---|---|---|
| 6,226,547 B1 | 5/2001 | Lockhart et al. |
| 6,235,038 B1 | 5/2001 | Hunter et al. |
| 6,246,898 B1 | 6/2001 | Vesely et al. |
| 6,373,240 B1 | 4/2002 | Govari |
| 6,574,498 B1 | 6/2003 | Gilboa |
| 6,690,963 B2 | 2/2004 | Ben-Haim et al. |
| 6,772,002 B2 | 8/2004 | Schmidt et al. |
| 6,796,943 B2 | 9/2004 | Mochizuki |
| 7,555,331 B2 | 6/2009 | Viswanathan |
| 7,720,520 B2 | 5/2010 | Willis |
| 8,057,487 B2 * | 11/2011 | Chu ............... A61B 90/11 606/130 |
| 8,249,689 B2 | 8/2012 | Anderson |
| 8,456,182 B2 | 6/2013 | Bar-Tal et al. |
| 8,494,614 B2 | 7/2013 | Markowitz et al. |
| 9,398,866 B2 | 7/2016 | Hauck et al. |
| 9,510,772 B2 | 12/2016 | Edwards |
| 9,789,029 B2 | 10/2017 | Besser et al. |
| 9,827,169 B2 | 11/2017 | Besser et al. |
| 9,839,584 B2 | 12/2017 | Nevler et al. |
| 9,974,615 B2 | 5/2018 | Woerlein et al. |
| 10,010,374 B2 | 7/2018 | Besser et al. |
| 10,286,228 B2 | 5/2019 | Bharat et al. |
| 10,314,658 B2 | 6/2019 | Gliner et al. |
| 10,350,145 B2 | 7/2019 | Besser et al. |
| 10,362,963 B2 | 7/2019 | Koyrakh et al. |
| 10,376,447 B2 | 8/2019 | Besser et al. |
| 10,426,350 B2 * | 10/2019 | Mihailescu .......... A61B 8/4438 |
| 10,506,946 B2 | 12/2019 | Byrd et al. |
| 10,548,815 B2 | 2/2020 | Cohen et al. |
| 10,646,406 B2 | 5/2020 | Nevler et al. |
| 10,695,269 B2 | 6/2020 | Besser et al. |
| D892,985 S | 8/2020 | Besser et al. |
| 2013/0066193 A1 | 3/2013 | Olson et al. |
| 2014/0051983 A1 * | 2/2014 | Schroeder ............... A61B 34/20 600/424 |
| 2016/0161241 A1 | 6/2016 | Li et al. |
| 2017/0071683 A1 | 3/2017 | Prosco et al. |
| 2017/0143589 A1 | 5/2017 | Besser et al. |
| 2018/0014751 A1 | 1/2018 | Hill et al. |
| 2018/0049810 A1 | 2/2018 | Besser et al. |
| 2018/0280093 A1 | 10/2018 | Besser et al. |
| 2019/0004122 A1 * | 1/2019 | Jung .................. G01R 33/0206 |
| 2019/0167366 A1 | 6/2019 | Ummalaneni et al. |
| 2019/0167531 A1 | 6/2019 | Besser et al. |
| 2019/0220976 A1 | 7/2019 | Holsing et al. |
| 2020/0046433 A1 | 2/2020 | Krimsky et al. |
| 2020/0121399 A1 * | 4/2020 | Besser .............. A61M 25/0158 |
| 2020/0155419 A1 | 5/2020 | Cohen et al. |

* cited by examiner

SYSTEM AND METHOD FOR DETECTING MEDICAL DEVICE LOCATION AND ORIENTATION IN RELATION TO PATIENT ANATOMY

CROSS-REFERENCE TO RELATED APPLICATIONS

The present application is a continuation of U.S. patent application Ser. No. 17/007,576 filed on Aug. 31, 2020, which is incorporated herein in its entirety by reference thereto.

FIELD OF THE INVENTION

The subject matter of the present invention relates generally to an electromagnetic system and method for detecting the location and orientation of a medical device in relation to a patient's anatomy.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These intravascular catheters include, among others, central venous catheters, peripheral venous catheters and the peripherally inserted central catheters. These catheters include a relatively small tube that passes through the patient's veins or arteries. Depending on the application, the health care provider can use an intravascular catheter to remove blood vessel blockages, place inserts into blood vessels and provide patients with injections of medications, drugs, fluids, nutrients, or blood products over a period of time, sometimes several weeks or more.

When using these known enteral and intravascular catheters, it is important to place the end of the catheter at the proper location within the human body. Erroneous placement of the catheter tip may injure or harm the patient. For example, if the health care provider erroneously places an enteral catheter into the patient's lungs, liquid may be introduced into the lungs with harmful results. If the health care provider erroneously places an intravascular catheter into the wrong blood vessel of the cardiovascular system, the patient may experience infection, injury or a harmful blockage.

With feeding tubes in particular, it is also prudent to check that the exit aperture of the feeding tube (typically located at the distal end/tip of the tube) remains in its desired location over the period of treatment, e.g., feeding. Protocols that address this requirement in enteral feeding tubes include frequent monitoring for the appropriate pH of fluids extracted from the feeding tube when not carrying nutritional liquids and careful patient monitoring to ensure nutritional uptake is as expected.

In some cases, health care providers use X-ray machines to gather information about the location of catheters within the body. There are several disadvantages with using X-ray machines. For example, these machines are relatively large and heavy, consume a relatively large amount of energy and expose the patient to a relatively high degree of X-ray radiation. Also, these machines are typically not readily accessible for use because, due to their size, they are usually installed in a special X-ray room. This room can be far away from the patient's room. Therefore, health care providers can find it inconvenient to use these machines for performing catheter insertion procedures. Furthermore, it can be inconvenient to transport these machines to a patient's home for home care catheter procedures. Moreover, even X-rays are not necessarily conclusive as to the location of the catheter tip, as the natural and continuous movement of the internal organs can make it difficult for the physician interpreting the X-ray to be sure of the actual location of the distal end of the catheter.

Another existing catheter locating means involves using an electromagnetic coil positioned inside the catheter and an electromagnetic coil locating receiver outside of the patient's body. The electromagnetic coil is generally incorporated into a stylet or guide wire which is inserted within the catheter. The coil locating receiver can be used to determine the distance the coil is from the receiver and its depth in the patient's body and can communicate with a display to show a reference image of a non-subject body and an image of the coil located on the display with the reference image. However, these systems also have several disadvantages. For example, the coil locating receiver is a large device that must rest in a precise location outside the patient's body and does not permit for adjustments due to each individual patient's anatomical size or shape. However, a patient undergoing a feeding tube placement will be agitated and sudden movements are expected, which can move the coil locating receiver, thus increasing the likelihood of positional errors or complications in locating the catheter. Additionally, these existing systems can only display the coil location over a reference image of a non-subject (i.e., a generic patient) body without reference to the individual patient's particular anatomy. Therefore, health care providers can estimate the positioning of the catheter using the electromagnetic coil and coil locating receiver but cannot estimate or view the specific patient's anatomy.

Consequently, there is a need for a medical device, e.g., catheter, position guidance system, that is adaptable to patients of all sizes to ensure more accurate catheter placement. In particular, a medical device position guidance system that provides a stationary frame of reference with the patient and determines patient anatomical shape and size would also be useful.

SUMMARY

Objects and advantages of the invention will be set forth in part in the following description, or may be obvious from the description, or may be learned through practice of the invention.

The present invention is directed to a medical device position guidance system. The system includes at least one reference transmitter, wherein the at least one reference transmitter is configured to maintain a fixed position relative to a subject. The system further includes a receiver system configured to receive signals from the at least one reference transmitter; a processor, wherein the at least one reference transmitter and the receiver system are operatively coupled to the processor; and a memory device. The memory device stores instructions which when executed by the processor, cause the processor to: (i) receive signals relating to the location and orientation of the receiver system relative to the at least one reference transmitter; and (ii) using the received signals, create an anatomical coordinate system.

In one particular embodiment, the medical device position guidance system can further include an inserted transmitter configured to be inserted into the subject, wherein the receiver system is configured to receive signals from the inserted transmitter. The memory device can store instructions which when executed by the processor, cause the processor to: (i) receive signals relating to the location and orientation of the inserted transmitter relative to the receiver system; and (ii) using the received signals relating to the location and orientation of the inserted transmitter relative to the receiver system, plot the location and orientation of the inserted transmitter on the anatomical coordinate system. Moreover, the inserted transmitter can be mounted to a catheter or mounted on a stylet configured to be inserted within a catheter. Further, the inserted transmitter can include at least one coil configured to generate electromagnetic signals, and the at least one coil can be a single-axis coil or a multi-axis coil.

In another embodiment, the system can further include at least one registration transmitter, wherein the registration transmitter is configured to be placed on an anatomical landmark of the subject, wherein the receiver system is configured to receive signals from the at least one registration transmitter. The memory device can store instructions which when executed by the processor, cause the processor to: (i) receive signals relating to the location and orientation of the at least one registration transmitter relative to the receiver system; (ii) using the received signals relating to the location and orientation of the at least one transmitter relative to the receiver system, plot the location and orientation of the registration transmitter on the anatomical coordinate system; and (iii) register the anatomical landmark on the anatomical coordinate system such that the anatomical coordinate systems forms a representation of the subject's external anatomy. Moreover, the memory device can further include information defining a pre-defined anthropometric relationship between the anatomical coordinate system of the subject's external anatomy and the internal anatomical shape and size of the subject. Further, the registration transmitter can include a secondary transmitter configured to provide additional information about the anatomy of the subject, and the secondary transmitter can include an ultrasound transducer.

In an additional embodiment, the system can include a display device operatively coupled to the processor; wherein the memory device stores instructions which when executed by the processor, cause the processor to cause the display device to display the anatomical coordinate system.

In a further embodiment, each reference transmitter can include a set of three coils oriented orthogonally to one another, wherein each of the coils is configured to transmit electromagnetic signals.

In another embodiment, the receiver system can include a sensor comprising a tri-axial coil configured to receive electromagnetic signals.

In yet another embodiment, the receiver system can be configured to be able to move relative to the at least one reference transmitter. Moreover, the receiver system can include at least two sensors configured to receive signals from the at least one reference transmitter. Further, each sensor of the receiver system can include an independent housing such that each sensor of the receiver system is in a dynamic spatial relationship relative to each other, or the at least two sensors can be enclosed in a unitary receiver housing.

The present invention is further directed to a method for medical device position guidance. The method includes steps of: securing at least one reference transmitter to a fixed anatomical landmark of a subject; generating an electromagnetic field using the at least one reference transmitter; sensing the electromagnetic field using a receiver system comprising at least one sensor; determining the location and orientation of the at least one sensor of the receiver system relative to the at least one reference transmitter; and creating an anatomical coordinate system.

In one particular embodiment, the method can further include a step of registering at least one anatomical landmark of the subject in the anatomical coordinate system such that the anatomical coordinate systems forms a representation of the subject's external anatomy. Moreover, the step of registering at least one anatomical landmark of the subject can include: (i) placing a transmitter on an anatomical landmark of the subject; (ii) generating an electromagnetic field using the transmitter; (iii) sensing the electromagnetic field using the receiver system; (iv) determining the location and orientation of the transmitter relative to the at least one sensor of the receiver system; (v) plotting the anatomical landmark in the anatomical coordinate system; and optionally repeating steps (i)-(v) for any additional desired anatomical landmarks. Further, the transmitter for the step of registering at least one anatomical landmark of the subject can be the reference transmitter, or a registration transmitter that is distinct from the reference transmitter. Moreover, the step of registering at least one anatomical landmark of the subject can include: (i) placing the receiver system on an anatomical landmark of the subject; (ii) generating an electromagnetic field using the reference transmitter; (iii) sensing the electromagnetic field using the receiver system; (iv) determining the location and orientation of the transmitter relative to the at least one sensor of the receiver system; (v) plotting the anatomical landmark in the anatomical coordinate system; and optionally repeating steps (i)-(v) for any additional desired anatomical landmarks. Further, the method can further include a step of using a pre-defined anthropometric relationship between the anatomical coordinate system of the subject's external anatomy to determine the internal anatomical shape and size of the subject within the anatomical coordinate system.

In an additional embodiment, the method can include steps of: generating an electromagnetic field using an inserted transmitter; sensing the electromagnetic field of the inserted transmitter using the at least one sensor of the receiver system; determining the location and orientation of the at least one sensor of the receiver system relative to the inserted transmitter; and plotting the location and orientation of the inserted transmitter on the anatomical coordinate system. Moreover, the step of registering at least one anatomical landmark of the subject can be performed by the inserted transmitter.

In another embodiment, the at least one sensor of the receiver system can be movable relative to the subject, wherein the method further comprises a step of periodically updating the location and orientation of the at least one sensor of the receiver system relative to the at least one reference transmitter. Further, the at least one sensor can be at least two sensors, further wherein each of the sensors is in a dynamic spatial relationship relative to each other. Moreover, the at least one sensor can be at least two sensors enclosed in a unitary housing such that the at least two sensors are in a static spatial relationship relative to each other.

In a further embodiment, the method can include a step of displaying the anatomical coordinate system on a display.

In yet another embodiment, the method can include steps of: providing a secondary transmitter configured to provide additional information about the anatomy of the subject; and combining data from the secondary transmitter about the anatomy of the subject with the anatomical coordinate system to create an anatomical map of the anatomy of the subject. Further, the secondary transmitter can include an ultrasound transducer configured to provide visualization of the anatomy of the subject.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
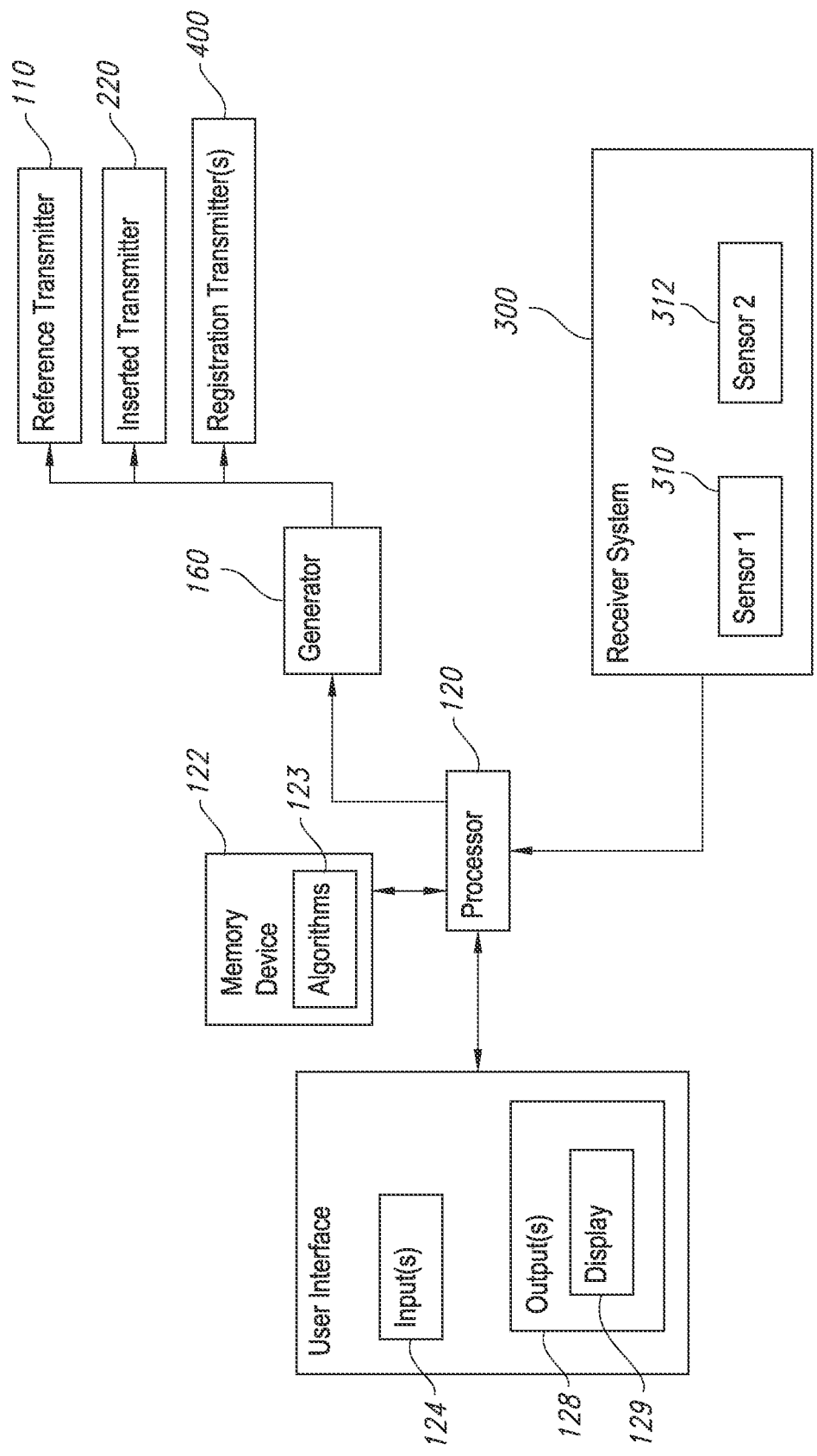
FIG. 1 illustrates a schematic diagram of a medical device position guidance system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a medical device position guidance system that aids in the placement of an invasive medical device (e.g., a catheter) inside a body of a subject/patient. The system detects the position and angle (pose) of a catheter or other invasive medical device in relation to a patient's anatomy and displays the information on a computer screen. For instance, the system can use a reference transmitter and a registration transmitter to register and scale a subject's anatomy. The reference transmitter can establish the "anchor" anatomical landmark around which the rest of the virtual anatomical structure is built, and the reference transmitter is fixed to the subject for continuous monitoring. Meanwhile, the registration transmitter can be used to modify (add and scale) the virtual anatomical structure and can be attached for continuous monitoring or used once during the setup of the system prior to insertion of the invasive medical device. Further, the system uses an inserted transmitter that is mounted on the invasive medical device to monitor placement of the catheter relative to virtual anatomical structure built by the reference transmitter and the registration transmitter. All of the transmitters in the system (e.g., the reference transmitter, the registration transmitter, and the inserted transmitter) can operate relative to a sensor (receiver system sensor that is placed near or on the body and which facilitates in placing the transmitters into the virtual anatomical structure (coordinate system) and relaying this information to the user. The present inventors have found that the use of a single receiver system that receives signals from each transmitter, e.g., the reference transmitter and the inserted transmitter, in combination with a reference transmitter having a fixed, known location on the patient's body, enables accurate determination of the location of the medical device and thus guidance of the placement of the medical device within the patient's body.

The present invention is directed to a medical device position guidance system. The system includes at least one reference transmitter, wherein the at least one reference transmitter is configured to maintain a fixed position relative to a subject. The system further includes a receiver system configured to receive signals from the at least one reference transmitter; a processor, wherein the at least one reference transmitter and the receiver system are operatively coupled to the processor; and a memory device. The memory device stores instructions which when executed by the processor, cause the processor to: (i) receive signals relating to the location and orientation of the receiver system relative to the at least one reference transmitter; and (ii) using the received signals, create an anatomical coordinate system. The present invention is further directed to a method for medical device position guidance. The method includes steps of: securing at least one reference transmitter to a fixed anatomical landmark of a subject; generating an electromagnetic field using the at least one reference transmitter; sensing the electromagnetic field using a receiver system comprising at least one sensor; determining the location and orientation of the at least one sensor of the receiver system relative to the at least one reference transmitter; and creating an anatomical coordinate system.

The specific features of the medical device position guidance system of the present invention may be better understood with reference to FIGS. 1-12.

Referring now to the drawings, FIG. 1 illustrates one embodiment of a medical device position guidance system 100. The medical device position guidance system 100 includes: (a) a console 150 that supports a controller or processor 120; (b) one or more input devices 124 for providing input signals to the system 100 such as one or more control buttons and/or a touch screen; (c) a memory device 122 including machine readable instructions and one or more computer programs (which, for example, may include a plurality of algorithms 123) which are used by the processor 120 to detect and communicate the position and angle of an invasive medical device 200 within a subject 10 (see FIGS. 2-3) based on information received from one or more transmitters which will be discussed in more detail below; (d) an electromagnetic generator 160; (e) one or more output devices 128, such as a display device 129 which indicate the information about the position and angle of the invasive medical device 200 to the health care provider; and (f) a power source 121 that is coupled to the console 150. In addition, the system further includes: (g) the invasive medical device 200 that includes an inserted transmitter 220; (h) one or more reference transmitters 110; (i) a receiver system 300 containing one or more sensors, e.g. sensors 310 and 312; (j) optionally, one or more registration transmitters 400, and/or (k) optionally, one or more secondary transmitters 410, where the one or more reference transmitters 110, the receiver system 300, the one or more registration transmitters 400, and the one or more secondary transmitters 410 are located external to the subject 10. Further, it is to be understood that the inserted transmitter 220, the one or more reference transmitters 110, the receiver system 300, the one or more registration transmitters 400, and/or the one or more secondary transmitters 410 can be electronically coupled to the processor 120 by a wire, cable, signal data connection, signal carrier or wireless connection and can be electrically coupled to the generator 160 by a wire, cable, or other suitable electric connection configured to transmit electromagnetic energy. Further, the receiver system 300 can be in communication with the reference transmitter 110, the inserted transmitter 220 of the invasive medical device 200, the one or more registration transmitters 400, and/or the one or more secondary transmitters 410.

Figure 2:
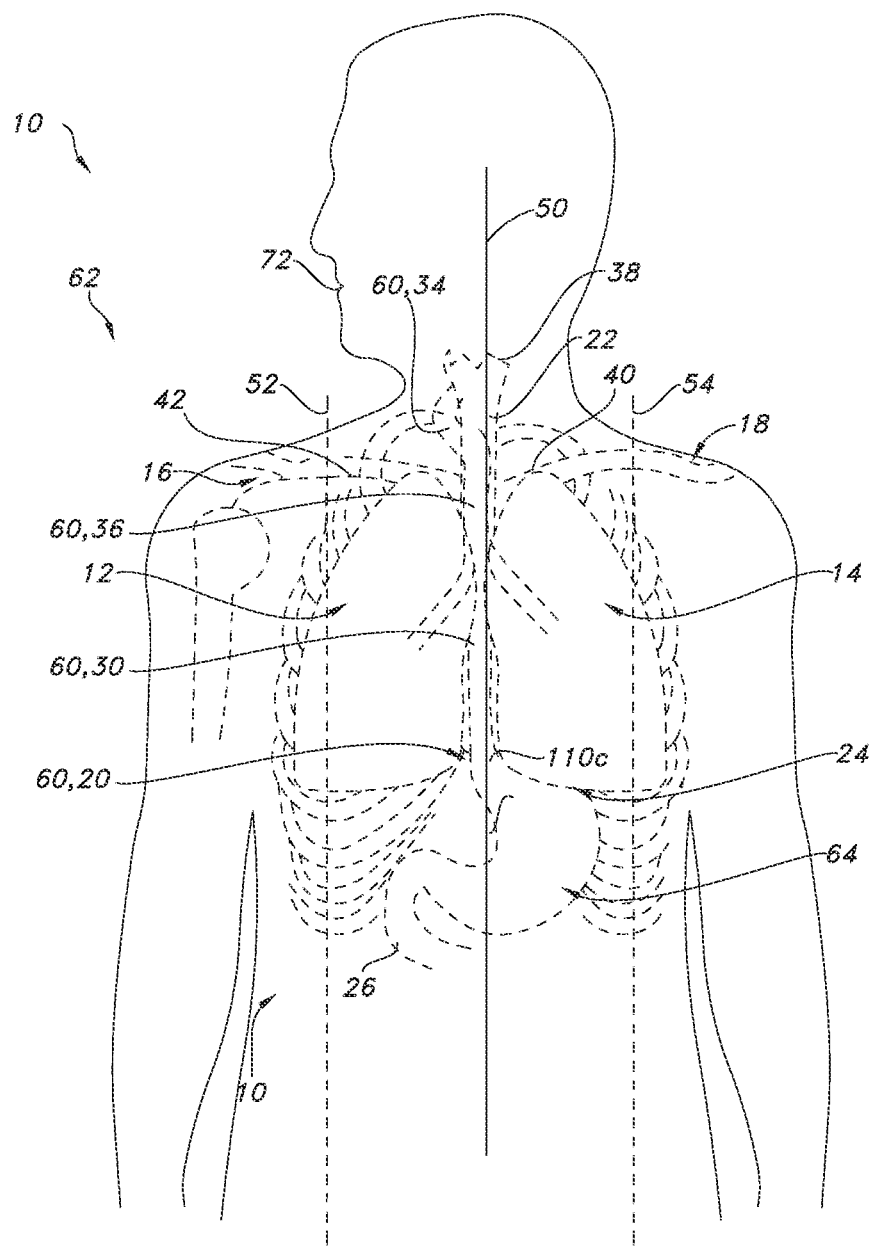
FIG. 2 illustrates anatomical landmarks of a human body.

FIG. 2 illustrates one or more various anatomical landmarks 60 of subject 10, which is a human body, where the anatomical landmarks 60 can be used in conjunction with the medical device position guidance system 100 to detect the position and angle (pose) of an invasive medical device 200 (e.g., a catheter) via the inserted transmitter 220 as well as the one or more reference transmitters 110, the one or more sensors, e.g., sensors 310 and 312 of the receiver system, the one or more registration transmitters 400, and the one or more secondary transmitters 410. However, although the illustrated example depicts a human, it should be appreciated that medical device position guidance system 100 could be used with any mammals such as domestic animals. When the medical device position guidance system 100 is used to determine a subject's upper anatomy such as for inserting an enteral catheter (feeding tube), the one or more reference transmitters 110, the receiver system 300, the one or more registration transmitters 400, and the one or more secondary transmitters 410 can be positioned on the subject 10, although it is not required that all the transmitters and receivers be positioned on the subject 10. It may be that only the one or more reference transmitters 110 is directly positioned on the subject 10. The one or more reference transmitters 110, receiver system 300, one or more registration transmitters 400, and/or the one or more secondary transmitters 410 can each be positioned at an anatomical landmark 60 that can include bony structures that may be visible or palpable from the external anatomy 62 of the patient including, but not limited to the right clavicle 16, the left clavicle 18, the xiphoid process 20, the sternum 20, one or more ribs 32, the jugular notch 34, the sternal angle 36, the mid-sagittal line 50, the right midclavicular line 52, the left midclavicular line 54, etc. As illustrated in FIG. 2, the xiphoid process 20 is the cartilaginous section at the lower end of the sternum 30 which is generally positioned along the mid-sagittal line 50 and which is not attached to any ribs 32 and is gradually ossified in adult humans. The right and left midclavicular lines 52 and 54 are each imaginary lines which are generally parallel to the mid-sagittal line 50 and pass downwards over the trunk of the human body 10 through the midpoint of the right and left clavicle bones 16 and 18, respectively. Further, there may be other points of the body to which the one or more reference transmitters 110, the receiver system 300 including one or more sensors 310, 312, the one or more registration transmitters 400, and/or the one or more secondary transmitters 410 could be reliably co-located or located with a predetermined offset for use in a reliable position guidance system 100. In any event, it is to be understood that such anatomical landmarks 60 palpable, visible, or locatable from the external anatomy 62 of the subject 10 can be used in conjunction with the inserted transmitter 220 to detect the position of the invasive medical device 200 with respect to the internal anatomy 64 of a subject 10 after it is inserted into the subject 10 via an orifice 72 (e.g., mouth) in, for instance, the esophagus 22, the stomach 24, the small intestine 26, the right lung 12, the left lung 14, the trachea 38, the left bronchus 40, the right bronchus 42, etc.

Figure 3:
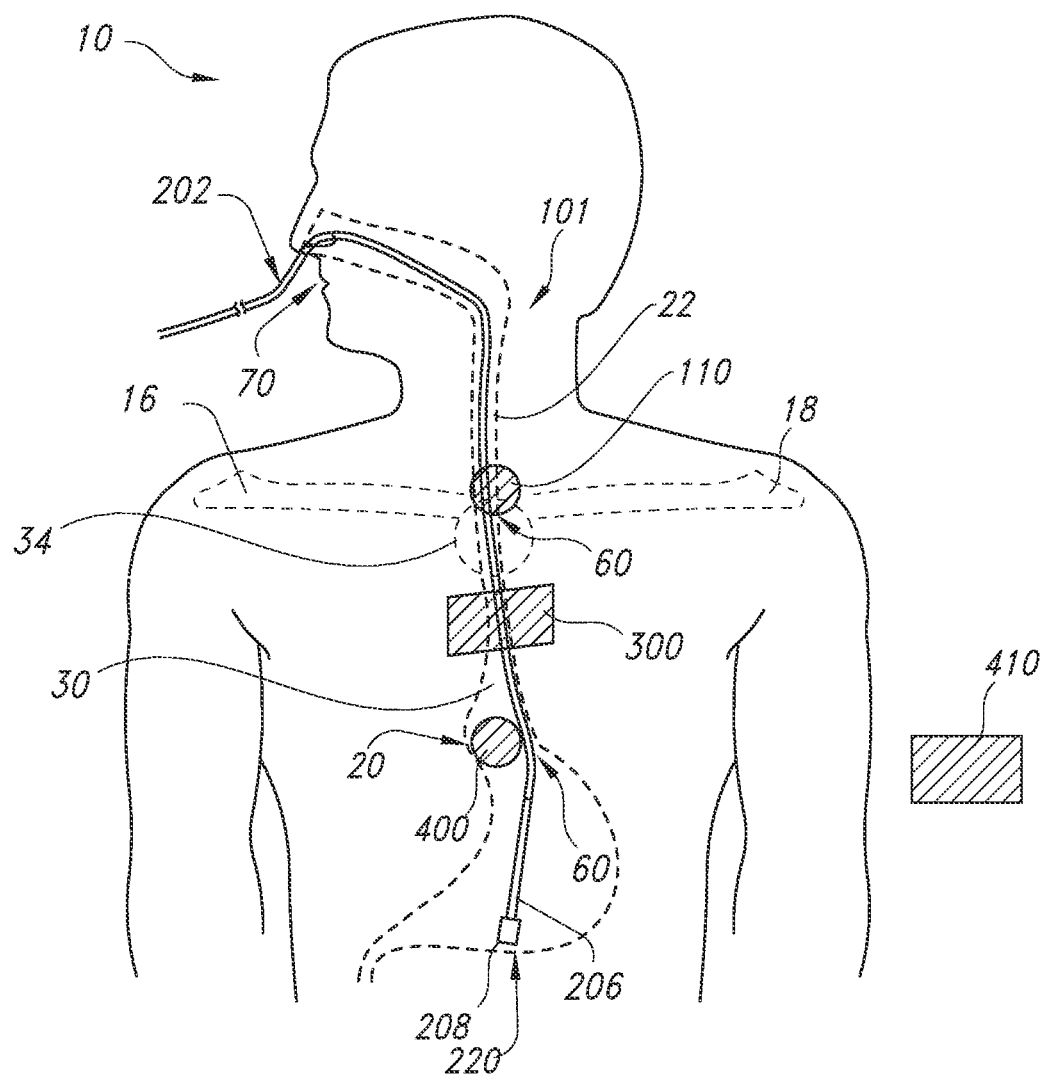
FIG. 3 illustrates a front view of the placement of the medical device position guidance system according to one embodiment of the present invention in relation to a subject's body.

In one particular embodiment, as shown in FIG. 3, which illustrates a front view of the placement of the medical device position guidance system 200 according to one embodiment of the present invention in relation to a subject 10's body is shown in which the xiphoid process 20 and the jugular notch 34 are used as the anatomical landmarks 60 when detecting the location of a tip 210 of an invasive medical device 200 such as a catheter within the subject 10's body after being inserted through orifice 72. As shown, a reference transmitter 110, which serves as a fixed anchor and generates an electromagnetic field covering the treatment area of the subject 10, can be positioned externally at an anatomical landmark 60 that is the jugular notch 34 located between the right clavicle 16 and the left clavicle 18. Further, in some embodiments (not shown), another reference transmitter 110 or a single reference transmitter 110 can be positioned at an anatomical landmark 60 that is the xiphoid process 20. Likewise, a registration transmitter 400, which is a magnetic field generator configured to register anatomical landmarks 60 on the subject 10, can be positioned externally at an anatomical landmark 60 that is the xiphoid process 20. jugular notch 34 located between the right clavicle 16 and the left clavicle 18. Further, in some embodiments (not shown), another registration transmitter or a single registration transmitter 400 can be positioned at an anatomical landmark 60 that is the jugular notch 34 located between the right clavicle 16 and the left clavicle 18. Moreover, the receiver system 300 can be movable but can be positioned along the sternum 30 between the jugular notch 34 and the xiphoid process 20, while a secondary transmitter 410 can also be positioned externally on the subject 10 or may be located near the subject 10 without being on the subject 10.

Figure 8:
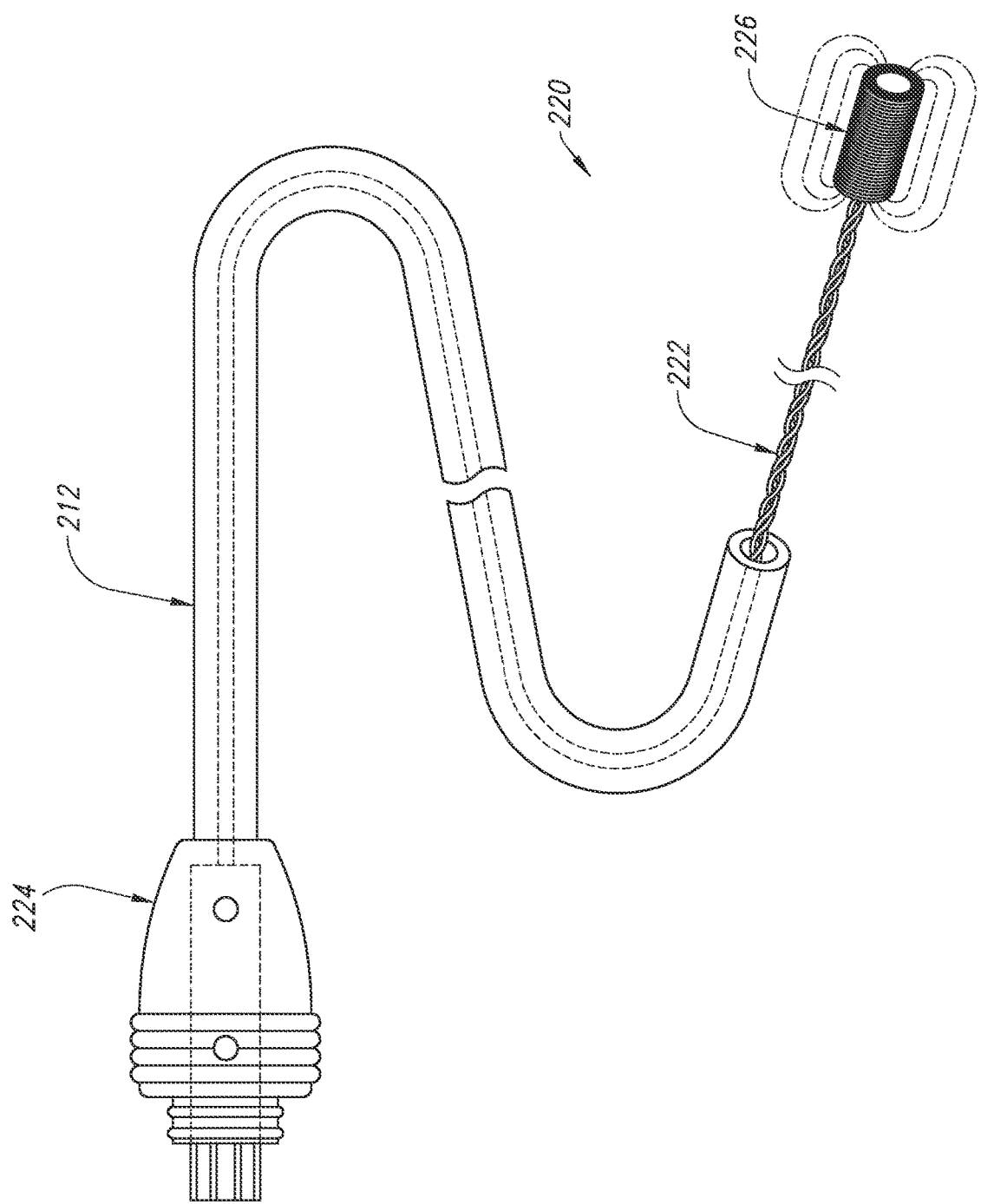
FIG. 8 illustrates a perspective view of the inserted transmitter of FIG. 7.

Referring now to the features of the inserted transmitter, 220, the one or more reference transmitters, 110, the one or more registration transmitters 400, the receiver system 300, and the one or more secondary transmitters 410 in more detail, the inserted transmitter 220, which is present in any suitable location on the invasive medical device 200, can be in the form of an electromagnetic field generator configured to be inserted into the body of the subject 10 such as via an orifice 72 (e.g., mouth). The inserted transmitter 220 generates an electromagnetic field covering the treatment area, or the area in which the invasive medical device 200 is to travel through and/or ultimately be positioned for treatment of the subject 10. The inserted transmitter 220 can be in the form of a single coil 226, as shown in FIG. 8, or a multi-axis coil, and in addition to being mounted on the invasive medical device 200 itself, it can also be mounted on a stylet and inserted into the lumen of the catheter 200. In one particular embodiment, the invasive medical device 200 can be a catheter in the form of a nasogastric tube as shown in more detail in FIG. 8.

Next, the one or more reference transmitters 110 can also be in the form of an electromagnetic field generator configured to be positioned on the subject 10's torso. The reference transmitter 110 can generate an electromagnetic field covering the treatment area, or the area in which the invasive medical device 200 is to travel through and/or ultimately be positioned for treatment of the subject 10 and serves to tie the coordinate system 101 created by the medical device position guidance system 100 to the subject, where the creation of the coordinate system 101 is discussed in more detail below with reference to FIGS. 9A-9E. The reference transmitter 110 can be located external to the body of the subject 10 and can also be in the form of a set of 3-axial orthogonal coils. The reference transmitter 110 serves as an anchor that compensates for the movement of the receiver system 300 in order to more accurately replicated the subject 10's internal anatomy 64 in the form of a virtual anatomic structure. With the aid of the one or more reference transmitter 110, the medical device position guidance system 110 is able to continuously discover the location of each of the sensors 310, 312 of the receiver system 300 in relation to the reference transmitter 110. Moreover, the reference transmitter 110 is responsible for establishing an anatomical coordinate system 101 for the subject, as discussed in more detail with respect to FIGS. 9A-9E. It is to be understood that in order to serve as an anchor for the medical device position guidance system 100 to accurately build the coordinate system 101 for each subject 10, when a single reference transmitter 110 is used, the reference transmitter 110 must generally remain static or stationary in rotation and position in relation to the anatomy of the subject 10.

However, it is also to be understood that the medical device position guidance system 100 can include two or more reference transmitters 110, where, for example, one reference transmitter 110 can be placed on the xiphoid process 20 and the other reference transmitter 100 can be placed on the jugular notch 34. For instance, two (or more) reference transmitters 110 can be used when the electromagnetic field generated by one or more of the reference transmitters 110 has a small range relative to the subject's anatomy and/or the detectable range of the receiver system 300. When two reference transmitters 110 are used then the relation between the first reference transmitters 110 and the second reference transmitter 110 can scale and orient the anatomical coordinate system 101, where each of the individual reference transmitters 110 are allowed to rotate but cannot move in relation to each other distance wise. Further, when two or more reference transmitters 110 are present in the system 100, the reference transmitters 110 can provide redundancy. For instance, the medical device position guidance system 100 can monitor the position of each reference transmitter 110 and issue an alarm if one or both of the reference transmitters 110 is moved. It should be understood that the reference transmitters 110 must be secured to the subject 10, such as via any suitable attachment means (adhesive, tape, hook and loop, etc.), as described in further detail below, in order to build an accurate visual anatomical structure via the system 100.

Next, the one or more registration transmitters 400 can be in the form of a field generator configured to register anatomical landmarks 60 on the subject 10 such as the jugular notch 34 or the xiphoid process 20. The one or more registration transmitters 400 can, when activated, generate a magnetic field covering the treatment area, or the area in which the invasive medical device 200 is to travel through and/or ultimately be positioned for treatment of the subject 10. The one or more registration transmitters 400 can be in the form of a single coil or a multi-axial coil assembly as well. If continuous monitoring is desired, the registration transmitter 400 can be mechanically attached to a particular part of the subject's body 10 such as an anatomical landmark 60. For instance, a housing having a fixation mechanism which can house the registration transmitter is described in further detail below with regard to FIGS. 5A-C. In addition, it is also to be understood that the one or more reference transmitters 110 can function similarly to a registration transmitter 400 and register relative to the location of the receiver system 300.

Additionally or alternatively, the coil 226 of the inserted transmitter 220 can function as a registration device and register anatomical landmarks relative to the location of the reference transmitter 110. For instance, a user can place the coil 226 of the inserted transmitter 220 on a known anatomical landmark 60 and initiate a registration process (e.g., push a button on the console 150) to register the anatomical landmark 60.

In addition, the receiver system 300, or an individual sensor (e.g., sensor 310 and/or 312) of the receiver system 300 (as described in further detail below), can function as a registration device and register anatomical landmarks relative to the location of the reference transmitter 110. For example, a user can point the corner of the receiver system 300 on the anatomical landmark 60 and push a button to register an anatomical landmark 60.

Figure 5A:
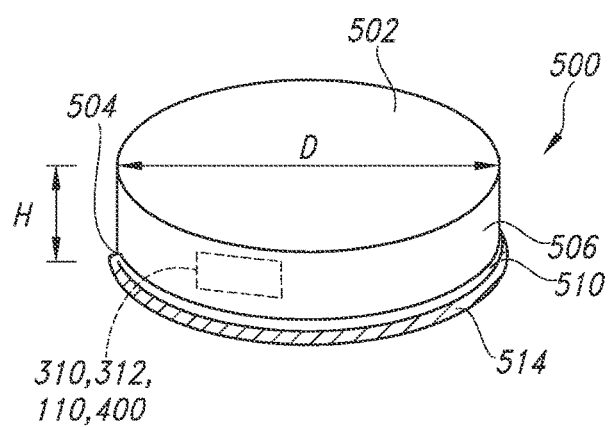
FIG. 5A illustrates a perspective view of a housing that can enclose a receiver system sensor, a reference transmitter or a registration transmitter of the medical device position guidance system of the present invention.

Meanwhile, the receiver system 300 includes one or more sensors, e.g., sensors 310 and 312 as shown in FIG. 1. The sensors 310 and 312 can be in the form of receivers that can receive an electromagnetic field. The receiver system 300 can detect the position of the inserted transmitter 220, the one or more reference transmitters 110, the one or more registration transmitters 400, and any other transmitter, such as a secondary general purpose transmitter 410 in some embodiments. It should be understood that each sensor 310, 312 of the receiver system 300 can sense along three orthogonal directions and can be in the form of a be tri-axial coil as shown in FIGS. 6A and 6B and as discussed in more detail below, or a tri-axial integrated circuit. In addition, the receiver system 300 can be composed of one physical unit, such as a unitary receiver housing 600 shown in FIG. 5D, enclosing the sensors 310, 312, or, alternatively, each of the sensors 310, 312 may have separate, i.e., distributed, housings 500 which are independently movable, as shown in FIG. 5A. When the sensors 310, 312 are each enclosed in independent distributed housings 500, the sensors 310, 312 are considered to be in a dynamic spatial relationship relative to each other Further, the medical device position guidance system 100 allows the receiver system 300 to move during placement, whether the receiver system 300 comprises a single unitary receiver housing 600 or a plurality of distributed housings 500. Although the receiver system 300 can be placed on the outside of the body of the subject 10, this is not required, and it is also possible for the receiver system 300 to be at or near the bedside of the subject 10.

As shown in the FIGS. 9A-9E, exemplary embodiments of the receiver system 300 of the present invention include two or more sensors such as sensors 310 and 312. When one or more of the transmitters, e.g., the inserted transmitter 220, include a single-axis coil, then two or more sensors are necessary to sense and determine the relative position of the single-axis transmitter coil. However, if all transmitters in the system 100 of the present invention are tri-axial electromagnetic coils, then the receiver system 300 may include a single sensor such as the sensor 310.

The present invention also contemplates the use of one or more secondary transmitters 410. The one or more secondary transmitters 410 can be described as general purpose transmitters and can contain a single set of 3-axial orthogonal coils and can be mounted on or inside any external components of the system 100 such that the position and the angle of the subject external component (e.g., reference transmitter 110, registration transmitter 400, receiver system 300) can be tracked by the system 100. The one or more secondary transmitters 410 function similarly to the registration transmitter 400 by registering a known anatomical landmark 60 in the anatomical coordinate system 101, while further providing additional information about the subject 10's anatomy that can be incorporated into an anatomical map combining the additional information with the anatomical coordinate system 101. In one particular embodiment, the secondary transmitter can be in the form of an ultrasound transducer, although any other suitable transmitter is contemplated by the present invention. The information obtained from the one or more secondary transmitters 410 (e.g., ultrasound images, etc.) can be merged with the position images built by the medical device position guidance system 100's anatomical coordinate system 101 utilizing the transmitters and receivers described above to enhance the virtual anatomical structure of the subject 10 and improve the accuracy of the system 100. When the secondary transmitter 410 is an ultrasound transducer, the system 100 can stitch together an ultrasound image of the subject 10's anatomy with the anatomical coordinate system 101 to provide a visualized anatomical map.

Figure 4:
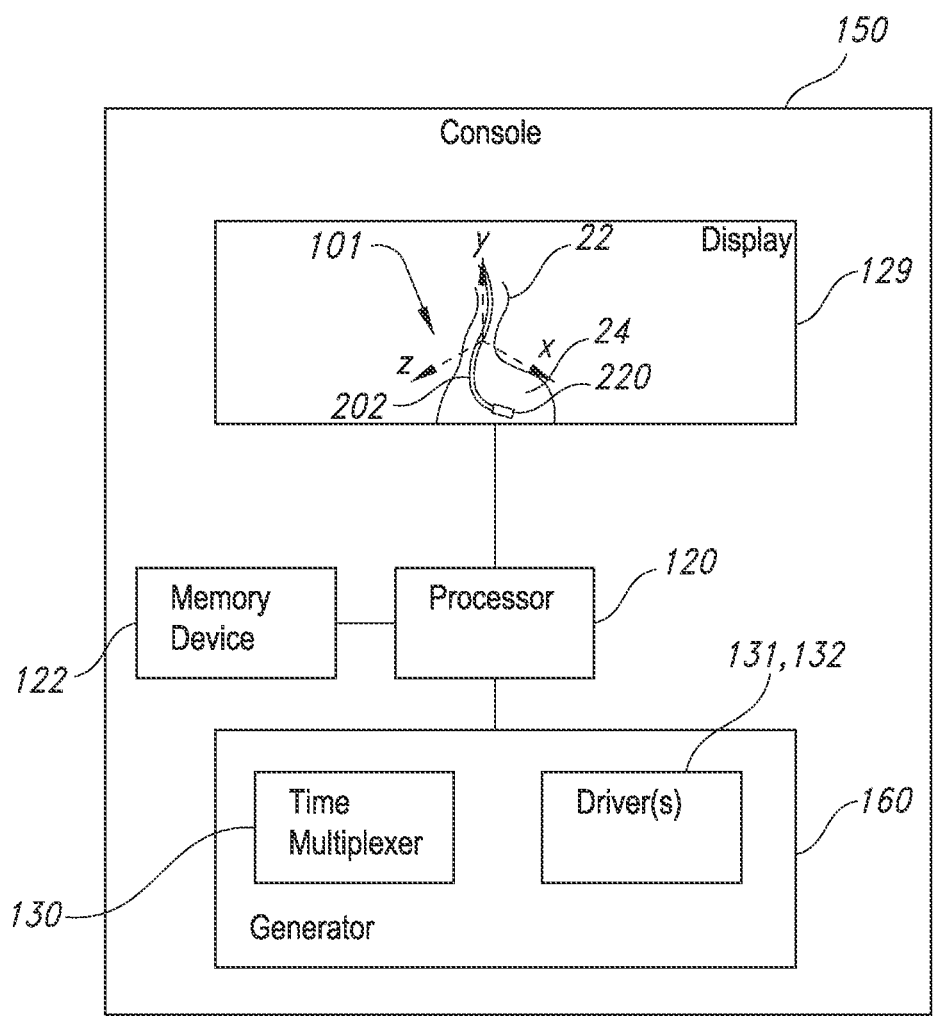
FIG. 4 illustrates a schematic diagram of a console that is part of the medical device position guidance system according to one embodiment of the present invention.

Next, FIG. 4 illustrates a schematic diagram of the console 150 that is part of the medical device position guidance system 100 as shown in FIG. 1 in more detail. As shown, in addition to the processor 120, memory device 122, and display 129 discussed above with respect to FIG. 1, the console 150 can also include the generator 150. The generator 150 can include a time multiplexer 130 and one or more coil drivers, such as coil driver 131 and coil driver 132. The coil drivers 131 and/or 132 are used to drive the inserted transmitter 220, the reference transmitter 110, and the registration transmitter 400 and are time multiplexed. In some embodiments, a single transmission frequency can be used via one of the coil drivers 131 or 132, as discussed in more detail in FIG. 10 where a single frequency driver is used. In this case, the time multiplexer is required to sequentially power each transmitter coil, e.g., the inserted transmitter 220 and each coil 113, 114, 115 of the tri-axial coil 112 of the reference transmitter. In other embodiments, multiple frequency drivers, e.g. frequency drivers 131 and 132, can be used, as discussed in more detail with respect to FIG. 11. FIG. 11 shows an example in which the single coil inserted transmitter 110 has a dedicated frequency driver 132, and the reference transmitter 110 having a tri-axial coil 112 is driven by combining a dedicated frequency driver 131 and a time multiplexer 130 to sequentially drive each of the tri-axial coils 113, 114, 115. When multiple frequency drivers are present, such as frequency drivers 131 and 132 shown in FIG. 11, each transmitter radiates electromagnetic energy at a unique frequency. This allows multiple transmitters (e.g., inserted transmitter 220 and reference transmitter 110) to be on and transmitting an electromagnetic frequency at the same time.

The receiver system 300 can include one or more housings 500, 600 to enclose the sensors 310, 312. For instance, both sensors 310, 312 can be disposed within a unitary receiver housing 600 (shown in FIG. 5D and described in further detail below) such that the sensors 310, 312 have a fixed distance between them. Alternatively, each sensor 310, 312 may be disposed in its own independent distributed housing, e.g., the distributed housing 500 illustrated in FIGS. 5A-C, such that each of the sensors 310, 312 can be independently movable, i.e., in a dynamic spatial relationship, relative to each other.

FIG. 5A illustrates a perspective view of a distributed housing 500. The distributed housing 500 can be configured to enclose a respective one of the sensors 310, 312 of the receiver system 300, a reference transmitter 110, or a registration transmitter 400. The distributed housing 500 can include an upper surface 502, a lower surface 504, and at least one side surface 506 extending from the upper surface 502 to the lower surface 504. For example, as shown in FIG. 5A, the upper surface 502 and the lower surface 504 can be circular or oval in shape and have a continuous side surface 506 extending therebetween, forming a generally cylindrical-shaped housing. In another embodiment (not shown), the upper surface 502 and the lower surface 504 can be polygonal, e.g., rectangular in shape and can have a plurality of side surfaces 506 extending therebetween corresponding to each of the sides of the polygonal housing. However, the external shape of the housing 500 is of little consequence to the way in which the receiver system 300, reference transmitter 110 or registration transmitter 400 functions. As such, the housing 500 can have any other suitable external shape based on a particular application of the medical device position guidance system 100.

The distributed housing 500 can have a footprint (i.e., shape and size of the lower surface 504) that is generally comparable to standard electrocardiogram leads. For example, the distributed housing 500 can have a diameter D extending across the widest portion of the upper surface 502 or lower surface 504 that is in a range from about 0.5 inches (1.25 cm) to about 5 inches (13 cm), or any value or range therebetween, such as from about 1 inch (2.5 cm) to about 3 inches (7.6 cm), for example from about 1.5 inches (3.8 cm) to about 2.5 inches (6.4 cm). The at least one side surface 328 of the housing 322 can have a height H in a range from about 0.25 inches (0.63 cm) to about 2 inches (5.1 cm), or any value or range therebetween, such as from 0.3 inches (0.76 cm) to about 1 inch (2.5 cm), for example about 0.5 inches (1.25 cm). In addition, the housing 500 can be lightweight.

Figure 5B:
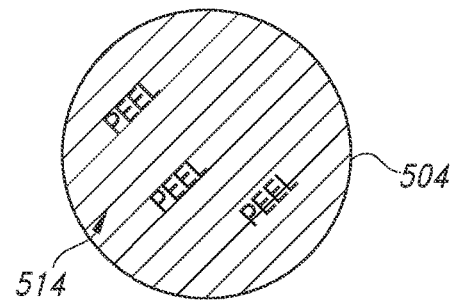
FIGS. 5B-C illustrate bottom views of the housing of FIG. 5A.
Figure 5C:
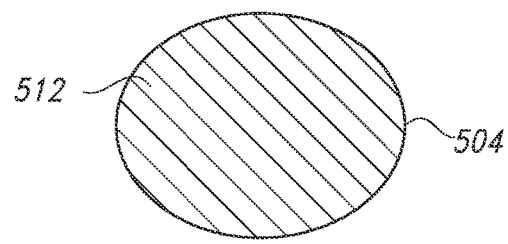

As shown in FIGS. 5A-C, each distributed housing 500 can further include a fixation mechanism 510 that is configured to affix the housing 500 to the subject. In a preferred embodiment, the distributed housing 500 can be directly affixed to the subject's body 10 by the fixation mechanism 510 so that the distributed housing 500, and thereby the enclosed sensor 310, reference transmitter 110, or registration transmitter 220, maintains a fixed reference point in relation to the subject 10. For instance, when the distributed housing 500 encloses a sensor 310 or 312 of the receiver system 300, the receiver system 300 maintains a fixed reference point in relation to the subject 10. Thus, when the subject 10 moves, the receiver system 300 moves with the subject 10 to maintain a static frame of reference with respect to the particular patient. The fixation mechanism 510 can be positioned on the lower surface 504 of the housing 500. For example, the fixation mechanism 510 can include an adhesive material 512 that is configured to affix the distributed housing 500 to the skin of the subject, a patch on the subject's body, or a garment worn by the subject. The adhesive material 512 can be an adhesive substrate that can be adhesive on both sides such that it adheres to the lower surface 504 of the housing 500 on one side and to a subject's body or garment on the other side. When the fixation mechanism 510 is adhesive material 512 adhered to the lower surface 504 of the housing 500, the housing 500 can additionally include a peelable protective sheet 514 covering the entire adhesive material 512. The peelable protective sheet 514 can be removed prior to affixing the adhesive 512 to the subject 10 or the subject's garment. Optionally, a used adhesive substrate 512 can be removed from the housing 500 and discarded, and a new adhesive substrate 512 can be applied. Alternatively, the adhesive material 512 can be any suitable adhesive arrangement which is capable of releasably adhering the housing 500 to the subject's skin or garment. In other embodiments, the fixation mechanism 500 can include a clip, pin, magnet, hook and loop system, or any other suitable means for affixing the distributed housing 500 to a subject's body or garment. By using a fixation mechanism 510 on each housing 500 that can affix the housing 500 to the subject's body or garment, the frame of reference of the sensor or transmitter enclosed within the housing 500 can remain stationary with the subject's body. Thus, the likelihood of positional errors when using the medical device position guidance system 100 can be reduced as compared to other guidance systems because there can be fewer complications arising due to movement of the subject's body.

Figure 5D:
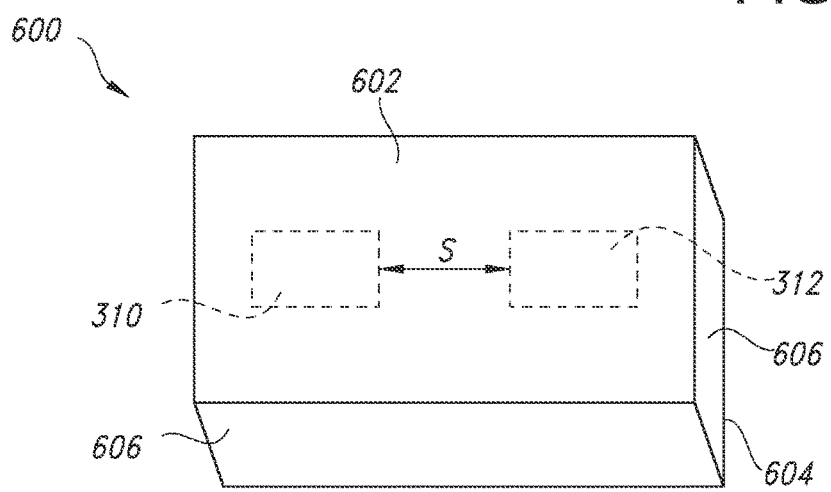
FIG. 5D illustrates a perspective view of a unitary receiver system housing that is configured to enclose two or more sensors of the receiver system.
Figure 6A:
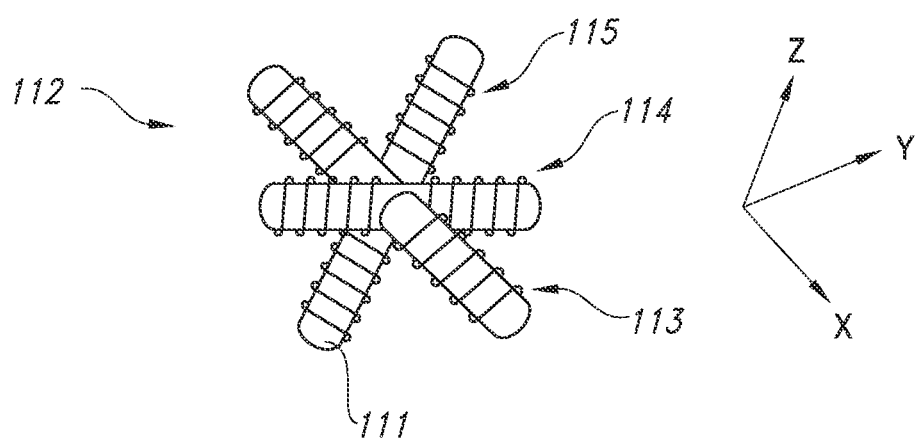
FIG. 6A illustrates a perspective view of a tri-axial electromagnetic coil of the present invention.
Figure 6B:
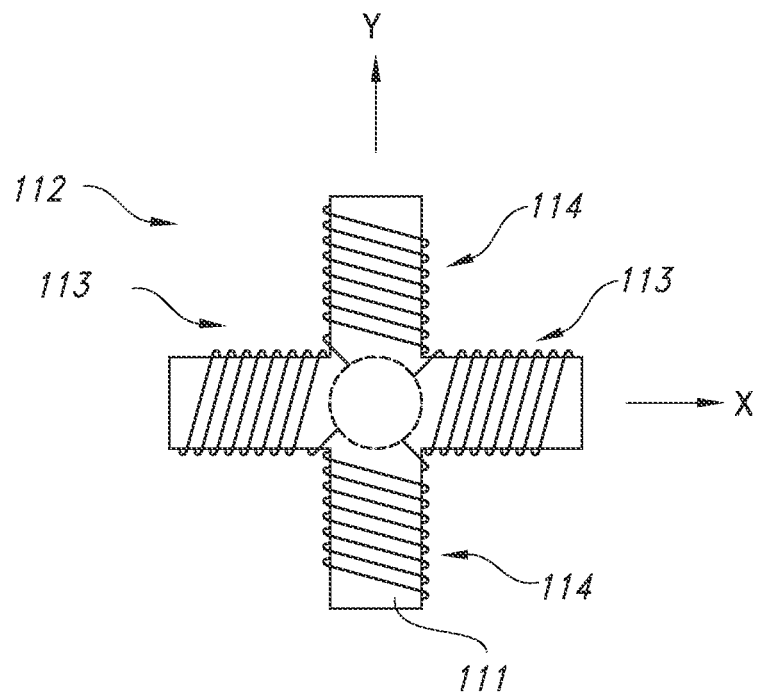
FIG. 6B illustrates a front view of the tri-axial electromagnetic coil of FIG. 6A.

Additionally or alternatively, as illustrated in FIG. 5D, the receiver system 300 can include a unitary receiver housing 600 that encloses one or more sensors, such as the sensors 310 and 312. The unitary receiver housing 600 can include an upper surface 602, a lower surface 604, and one or more side surfaces 606 such as four side surfaces as shown in FIG. 5D. The sensors 310 and 312 are enclosed within the housing 600. When the sensors 310 and 312 are enclosed within a unitary receiver housing 600, the sensors 310 and 12 may be spaced apart a fixed distance S within the housing 600 so that the sensors 310, 312 are in a static spatial relationship relative to each other. Moreover, although not shown in FIG. 5D, the unitary receiver housing 600 can optionally include a fixation mechanism 514 as described above with respect to the distributed housing 500.

As mentioned above, one or more of the transmitters and sensors of the system 100 can be in the form of a multi-axial coil. FIG. 6A illustrates a perspective view of a tri-axial electromagnetic coil of the present invention. FIG. 6B illustrates a front view of the tri-axial electromagnetic coil of FIG. 6A, illustrating the cross-shaped coil form 111. As shown, the tri-axial coil 112 includes a plurality of transmitter and/or receiver coils depending on the intended function that are arranged in an orthogonal orientation, i.e., disposed at right angles to each other. The tri-axial coil 112 include an x-axis coil 113, a y-axis coil 114, and a z-axis coil 115. In some embodiments, as shown in FIGS. 6A and 6B, the coils 113, 114, and 115 are disposed on a three-dimensional cross-shaped coil form 111 on which are wound the orthogonal coils 113, 114, and 115. FIG. 6B illustrates a view of the tri-axial coil assembly 112 in a horizontal plane such that x-axis coil 113 and the y-axis coil 114 are visible. However, any other suitable manner for constructing the tri-axial coil assembly 112 is contemplated by the present invention such that the coil assembly 112 can be in operative communication with the processor 120 via a data cable, microcoaxial cable, wireless data connection, or any other suitable means for sending and receiving signals regarding the coordinate system 101 and position and orientation or angle (pose) of the invasive medical device 200 with respect to the coordinate system 101 built by the combination of transmitters and sensors to the processor 120.

Figure 7:
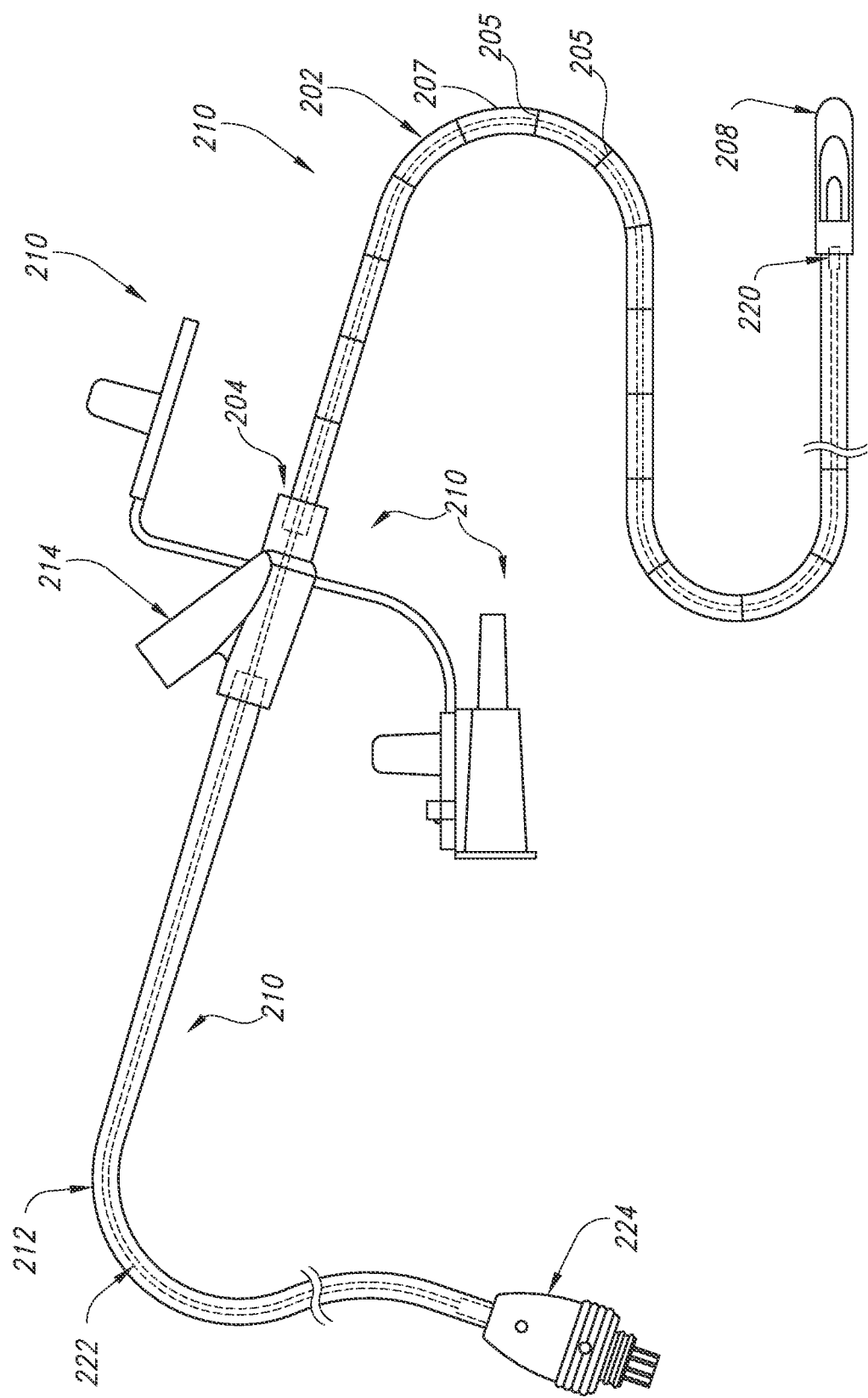
FIG. 7 illustrates a perspective view of an invasive medical device assembly having an inserted transmitter according to one embodiment of the present invention.

FIG. 7 illustrates a perspective view of an invasive medical device 200 having an inserted transmitter 220 according to one embodiment of the present invention. As mentioned above, the medical device position guidance system 100 can additionally include an invasive medical device 200 having an inserted transmitter 220. For example, in the embodiment illustrated in FIG. 7, the invasive medical device 200 can include a catheter 202 that is suitable for enteral nutrition having at least one lumen (passageway extending from the proximal end 204 to the caudal/distal end 206) or multiple lumens. In one embodiment, the catheter 202 can include markings 205 on the outer wall 207 of the catheter 202 indicating the length of the catheter 202 that has been inserted. An electromagnetic inserted transmitter 220 can be located near the tip of the catheter. The electromagnetic inserted transmitter 220 can be in the form of a coil 226 (see FIG. 8) adjacent to or embedded within the wall 207 of the catheter 200. The electromagnetic inserted transmitter 220 is operatively connected to the processor 120, for example, by at least one wire, cable, cord or electrical extension 222, or other wireless connection (not shown). For example, the electromagnetic inserted transmitter 220 can connect to a wire or pair of wires 222 which run the length of the catheter 202. In one embodiment, the pair of wires 222 can be incorporated into a metal stylet (not shown) used for inserting the catheter 202 into the subject's gastrointestinal tract. The pair of wires 222 includes at least one signal-carrying wire and can be bound together at the ends of the wires and may be encapsulated in material known to be suitable for its intended use. In a wireless embodiment, the electromagnetic inserted transmitter 220 can connect via wire(s) to the processor 120, which can then wirelessly receive and/or output information through any suitable wireless communication means, such as receiving and/or sending information through an antenna in the form of modulated electromagnetic waves or radio waves to an antenna on the console 150.

As shown in FIG. 7, the invasive medical device can include the catheter 202 as described above, in conjunction with a multi-port connector 214 and an electrical insulating tube 212 to form a tubing assembly 210. The electrical cable 222 and electrical insulating tube 212 can be attached to an electrical connector 224 at an end opposite the connector 214 and catheter 202. The electrical connector 224 is configured to electrically connect the inserted transmitter 220 to the generator 160, e.g., in the console 150.

The various methods contemplated by the present invention in which the medical device position guidance system 100 can build an anatomical coordinate system 101 to detect the position and angle (pose) of an invasive medical device 200 using the components discussed above with respect to FIGS. 1-8 will now be discussed in more detail with respect to FIGS. 9A-9E, as well as FIGS. 10-11.

First, a user (e.g., healthcare provider) can fix or secure a reference transmitter 110 on the body of the subject 10. Specifically, the reference transmitter 110 can be fixed on a location that minimizes movement in relation to the external anatomy 62 of interest. For example, the reference transmitter 110 can be fixed to an anatomical landmark such as the jugular notch 34, the sternal angle 36, or the xiphoid process 20 (see FIGS. 2-3). The reference transmitter 110 establishes an "anchor" anatomical landmark 60 around which the rest of the virtual anatomical structure, i.e., the anatomical coordinate system 101, will be built. Then, the user can place the receiver system 300, e.g., a sensor 310 enclosed within a distributed housing 500 or a unitary receiver housing 600 enclosing one or more sensors 310, 312, within the electromagnetic field generated by the reference transmitter 110. For instance, the receiver system 300 can be placed on the subject 10 or near the subject 10 (e.g., at the patient's bedside).

Figure 9A:
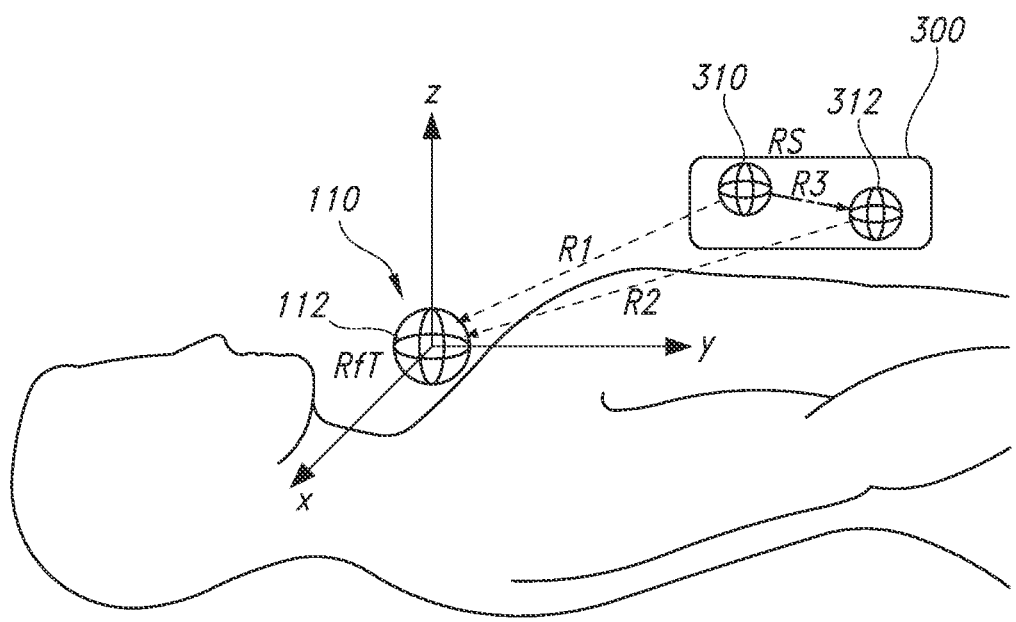
FIG. 9A illustrates a diagram of an anatomical coordinate system according to one embodiment of the medical device position guidance system.

Next, and referring to FIG. 9A, the sensors 310, 312 of the receiver system 300 can sense the electromagnetic field generated by the reference transmitter 110. Specifically, as shown in FIG. 9A, the system 100 can discover the pose (e.g., location and orientation/angle) of each sensor of the receiver system 300 relative to the reference transmitter 110 to develop the anatomical coordinate system 101. As shown in FIG. 9A, a distance referred to as vector R1 is calculated from the first sensor 310 to the reference transmitter 110 and distance referred to as vector R2 is calculated from the second sensor 312 to the reference transmitter 110. Each of the vectors R1 and R2 can have x, y, and z components. An anatomical coordinate system 101 is established, where the reference transmitter is considered the origin of the anatomical coordinate system 101. From the vectors R1 and R2, a distance and orientation between the sensors 310 and 312 can be calculated, referred to as vector R3.

Figure 9B:
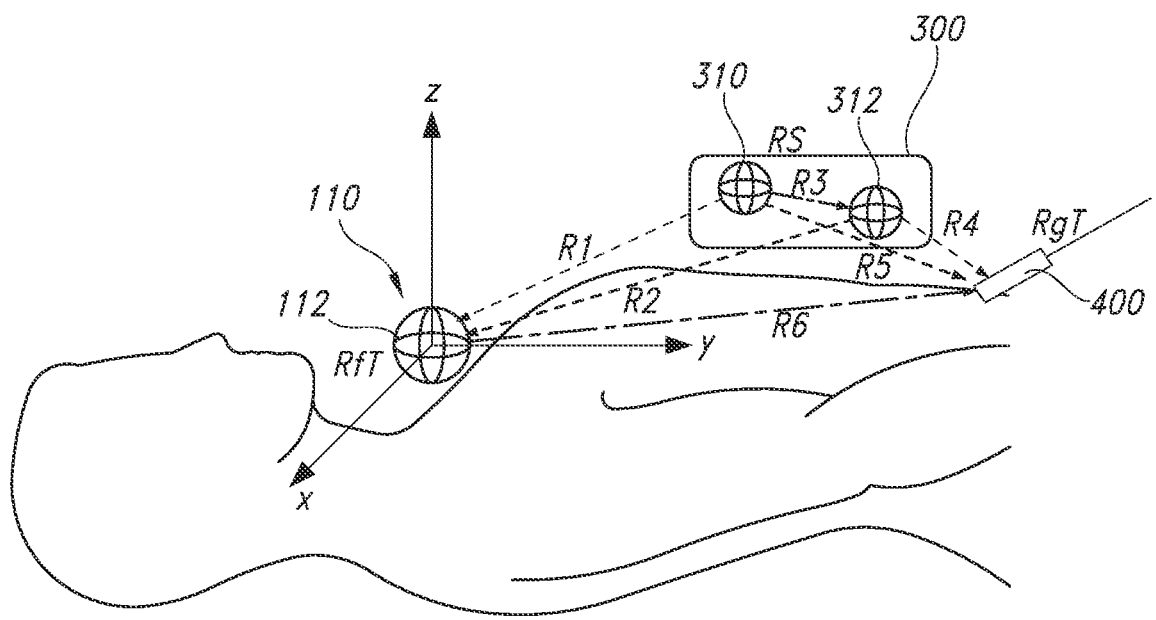
FIG. 9B illustrates a diagram of the anatomical coordinate system of FIG. 7A further including a registration transmitter according to one embodiment of the medical device position guidance system.
Figure 9C:
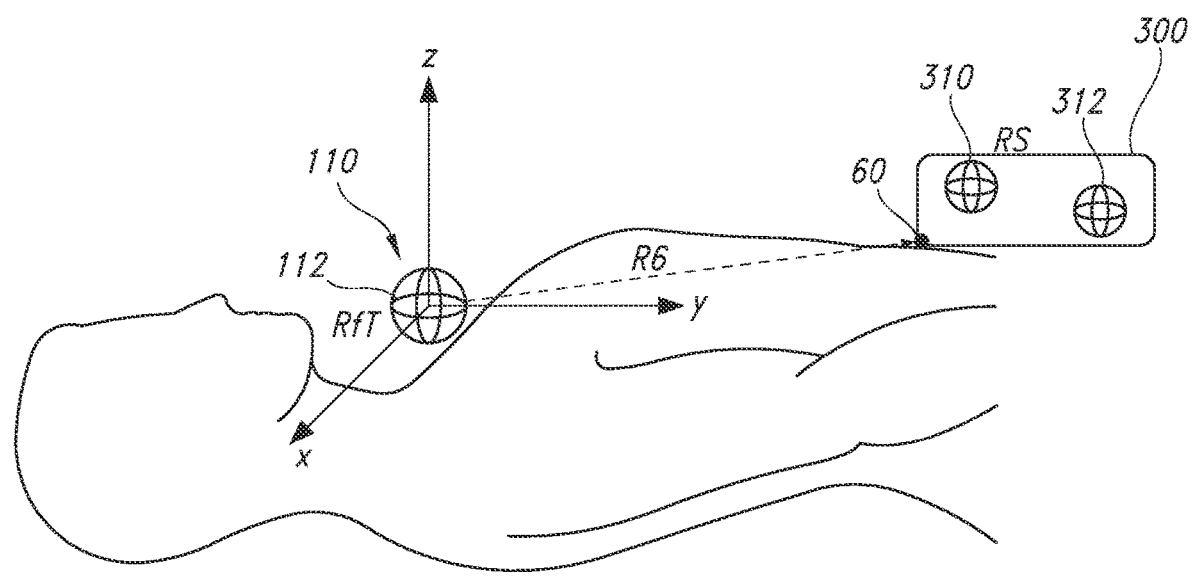
FIG. 9C illustrates a diagram of the anatomical coordinate system according to one embodiment of the medical device position guidance system in which the receiver system is used to register an anatomical landmark.

Referring to FIG. 9B, at least one registration transmitter 400 can be used to register one or more anatomical landmarks 60 such as the jugular notch 34, the sternal angle 36, or the xiphoid process 20 (see FIGS. 2-3). The registration of one or more anatomical landmarks 60 with the registration transmitter 400 can be used to build or add additional virtual anatomical structure in relation to the "anchor" point of the reference transmitter 110, thereby establishing an in-scale virtual anatomical structure. As shown in FIG. 9B, a distance referred to as vector R4 is calculated from the first sensor 310 to the registration transmitter 400 and distance referred to as vector R5 is calculated from the second sensor 312 to the registration transmitter 400. From the vectors R1, R2, R4 and R5, a distance between the reference transmitter 110 and the registration transmitter 400 an be calculated, referred to as vector R6. Using the distance of R6 between the reference transmitter 110 and the registration transmitter 400, which are each positioned at known anatomical landmarks on the body of the subject 10, the anatomical coordinate system 101 becomes an in-scale coordinate system of the anatomy of the subject 10.

Figure 9D:
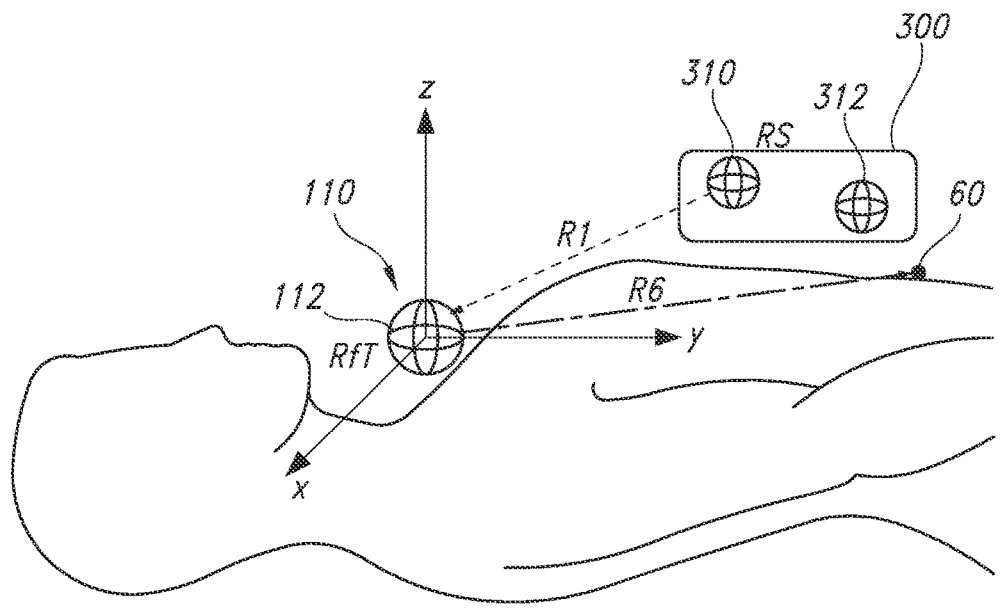
FIG. 9D illustrates a diagram of the anatomical coordinate system of FIG. 7C in which the receiver system is movable relative to the reference transmitter.
Figure 9E:
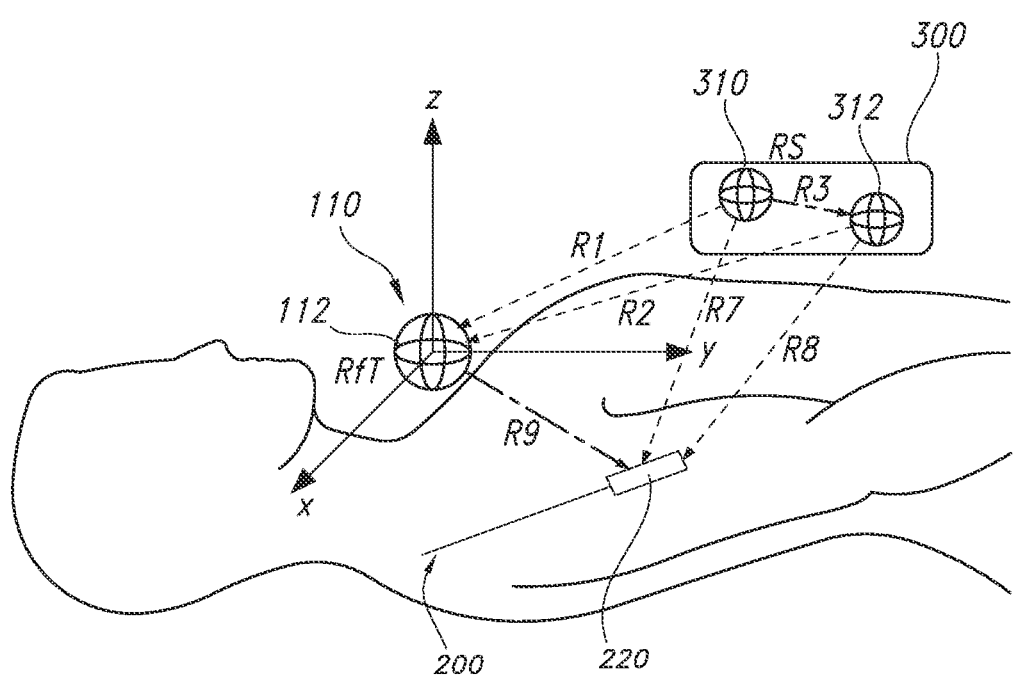
FIG. 9E illustrates a diagram of the anatomical coordinate system further including an inserted transmitter according to one embodiment of the medical device position guidance system.

Additionally or alternatively, the in-scale anatomical coordinate system can be developed by using the receiver system 300 in a 'registration mode' to register one or more anatomical landmarks 60. For instance, the receiver system, e.g., a housing 500 enclosing a sensor 310 of the receiver system 300, can be placed at a known anatomical landmark 60 such as the jugular notch 34, the sternal angle 36, or the xiphoid process 20 (see FIGS. 2-3). More particularly, a specific point, e.g., a corner, of the housing 320 can be placed at the landmark 60. The system 100 can be placed into registration mode, e.g., by pressing a button, and the distance from the reference transmitter 110 to the landmark 60 can be calculated, denoted by vector R6 in FIG. 9C. Then, as shown in FIG. 9D, the receiver system 300 can be moved away from the landmark 60 while the system 100 maintains a memory of the position of the landmark 60. Similarly to that described above with regard to FIG. 9B using a registration transmitter 400, the registration of one or more landmarks 60 using the receiver system 300 enables the anatomical coordinate system 101 becomes an in-scale coordinate system of the anatomy of the subject 10.

Moreover, it is to be understood that the present invention further contemplates embodiments in which both a registration transmitter 400 and the receiver system 300 can be used to register one or more anatomical landmarks 60 of the subject 10. In some aspects, the inserted transmitter 220 may also be used to register one or more anatomical landmarks 60 of the subject 10. Additionally or alternatively, the registration transmitter 400 may be used continuously, e.g., to detect movement of the subject's body 10 during a procedure. When both the reference transmitter 110 and the registration transmitter 400 are affixed to the subject's body 10, any change in the distance R6 between the reference transmitter 110 and the registration transmitter 400 can indicate movement of the subject's body 10.

Based on the location information detected as described above, the system 100 can construct an anatomical coordinate system 101 (see FIG. 3) against the external anatomy 62 and the internal anatomy 64 of the subject 10. For instance, in one embodiment, the system 100 can register an anatomical landmark 60 by having a user place a registration transmitter 400 on an anatomical landmark on the subject 10, where the position of the anatomical landmark 60 is recorded and can be but is not limited to the jugular notch 34 of the xiphoid process 20. Alternatively, the position of the reference transmitter 110 can be used as an anatomical landmark 60. Further, the system 100 can repeat this process and register multiple anatomical landmarks 60. Moreover, the system 100 utilizes the positions of the anatomical landmarks 60 and orients and scales the coordinate system 101 based on the specific positions for each individual subject 10 to provide accurate location information regarding the position of the invasive medical device 200. Then, the system 100 fixes the coordinate system 101 to the reference transmitter 110, where the coordinate system 101 is moved in relation to the subject 10 if the reference transmitter 110 moves.

Figure 12:
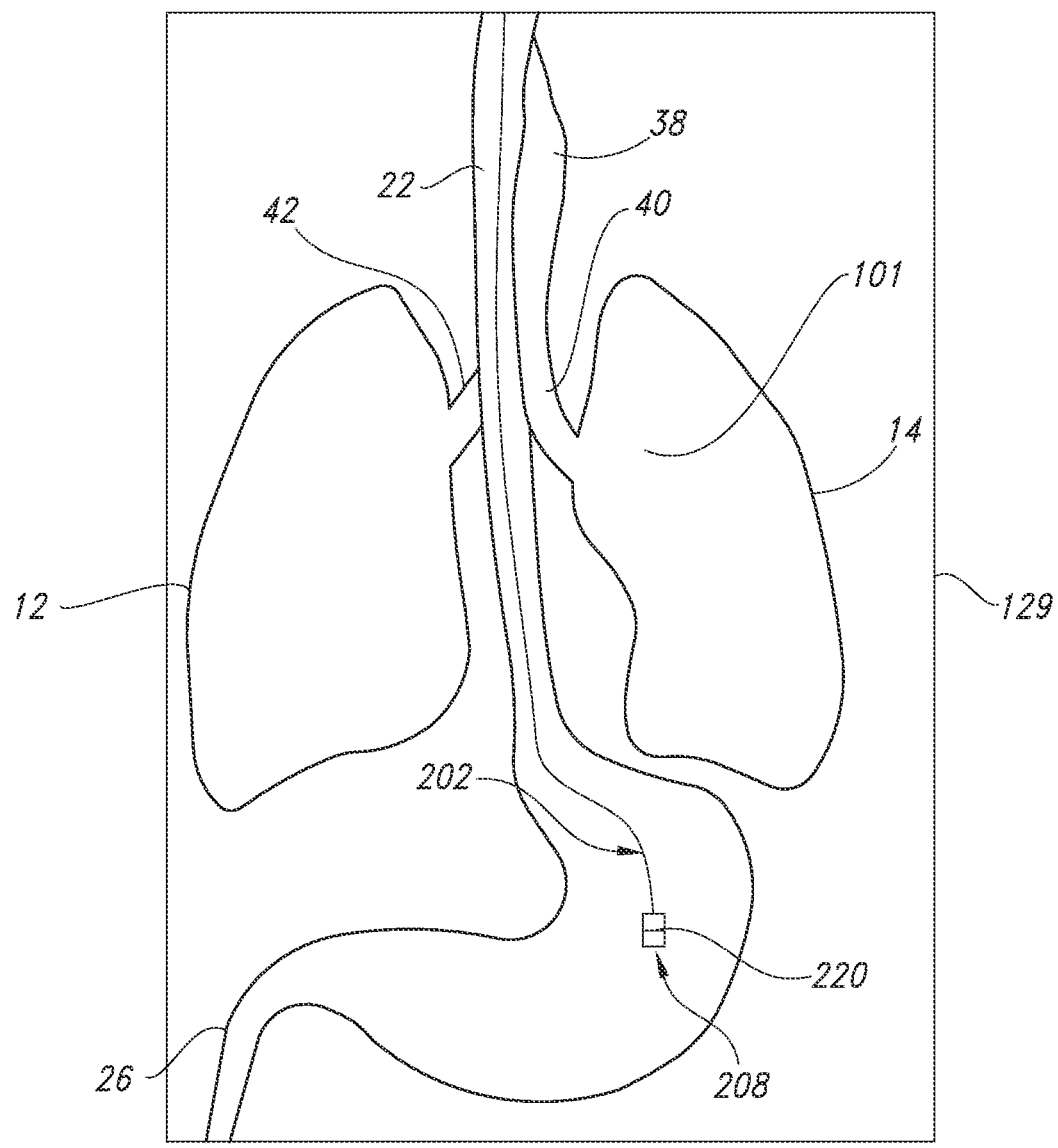
FIG. 12 illustrates the in-scale anatomical diagram created using the subject coordinate system according to one embodiment of the medical device position guidance system.

Next, the system 100 can detect the specific location and orientation of the inserted transmitter 220 relative to the anatomical coordinate system 101, where a user inserts the inserted transmitter 220 into the patient, then records the position and location of the inserted transmitter 220 in relation to the coordinate system 101. Specifically, a distance referred to as vector R7 is calculated from the first sensor 310 to the inserted transmitter 220 and a distance referred to as vector R8 is calculated from the second sensor 312 to the inserted transmitter 220. Then, the distance from the inserted transmitter 220 to the reference transmitter 110 can be calculated, which is shown as vector R9 in FIG. 9E. Using vector R9, the pose (i.e., location and orientation) of the inserted transmitter 220 can be plotted in the anatomical coordinate system 101. The system 100 then plots the position and angle of the inserted transmitter 220, the registration transmitter 400, the reference transmitter 110, and/or the receiver system 300 on a display device 129 as shown in FIG. 12. As shown, an outline of the internal anatomy 64, the external anatomy 62, and the anatomical landmarks 60 can be plotted on the display device 129, where the registered anatomical landmarks 60 can be used to project an outline of the internal anatomy 64. The inserted transmitter 220 is used to monitor the placement of the catheter 202 relative to the virtual anatomical structure, i.e., the anatomical coordinate system 101, that is built by the reference transmitter 110 and the registration transmitter 220. The location and orientation of the inserted transmitter 220 may be continuously monitored by the receiver system 300, for instance continuous monitoring throughout a catheter insertion procedure. Additionally, the location and orientation of the receiver system 300 relative to the reference transmitter 110 may be continuously monitored, as described above. When the receiver system continuously monitors the location and orientation of both the reference transmitter 110 and the inserted transmitter 220, movement of the receiver system 300, e.g., movement of the unitary housing 600 or the distributed housings 500, does not affect the calculated vector R9 of the inserted transmitter 220 in relation to the reference transmitter 110.

Figure 10:
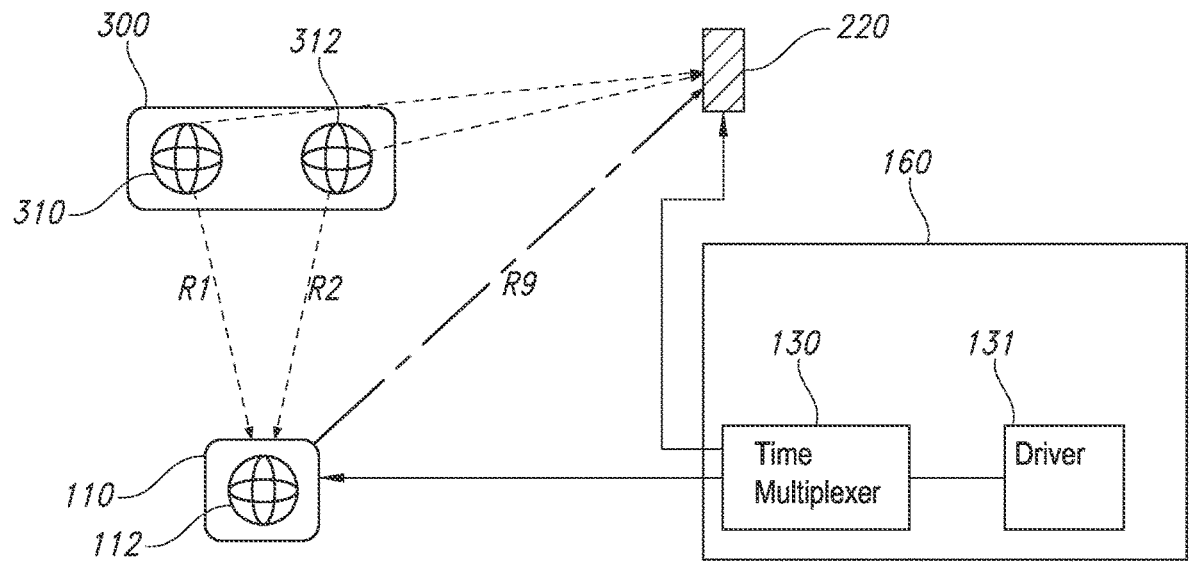
FIG. 10 illustrates a diagram of the medical device position guidance system of the present invention in use to determine the distance from a reference transmitter to the receiver system and from an inserted transmitter to the receiver system and having a single frequency driver.
Figure 11:
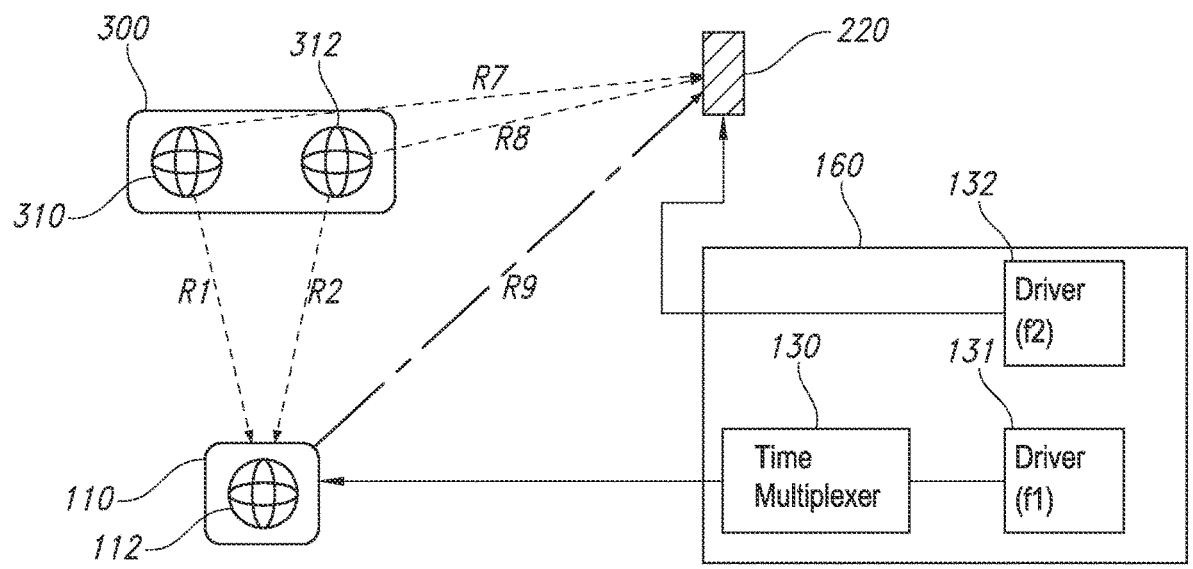
FIG. 11 illustrates a diagram of the medical device position guidance system of the present invention in use to determine the distance from a reference transmitter to the receiver system using a first frequency driver and from an inserted transmitter to the receiver system using a second frequency driver.

Turning now to FIGS. 10 and 11, the hardware and electronics configuration for the inserted transmitter 220, the reference transmitter 110, and the registration transmitter 400 are described in more detail. FIG. 10 illustrates a diagram of the medical device position guidance system 100 of the present invention in use to determine the distance referred to as vector R1 and vector R2 from a reference transmitter 110 to each of the sensors 310, 312 of the receiver system 300, respectively, and a distance referred to as vectors R7 and R8 from an inserted transmitter 220 to the each of the sensors 310, 312 of the receiver system 300, respectively. For instance, the reference transmitter 110 may be a tri-axial coil and the inserted transmitter 220 may be a single-axis coil. The electromagnetic fields generated by the reference transmitter 110 and the inserted transmitter 220 are generated by the generator 160 having a time multiplexer 130 and a single frequency driver 131. When using a single frequency driver 131, the time multiplexer 130 can instruct the frequency driver 131 to utilize a first frequency waveform to drive the x-axis coil 113 of reference transmitter 110, a second frequency waveform to drive the y-axis coil 114 of reference transmitter 110, a third frequency waveform to drive the z-axis coil 115 of reference transmitter 110, and a fourth frequency waveform to drive the single coil of the inserted transmitter 220.

FIG. 11 illustrates a diagram of the medical device position guidance system 100 of the present invention in use to determine the distance from a reference transmitter 110 to a receiver system 300 using a first frequency driver 131 and a distance from an inserted 220 transmitter to the receiver system 300 using a second frequency driver 132. In such an arrangement, the first frequency driver 131 and the second frequency driver each have a unique frequency as generated by the generator 160, where the first frequency driver 131 can be used to measure the distance associated with vectors R1 and R2 and the second frequency driver 132 can be used to measure the distance associated with vectors R7 and R8 when mapping the anatomical coordinate system 101. Further, whether a single frequency driver 131 or a first frequency driver 131 and a second frequency driver 132 is used, multiple frequency waveforms can be used within the drivers to for each coil in the transmitters. For instance, if the inserted transmitter 220 includes a single coil, a single frequency can be used for that specific coil. In the embodiment shown in FIG. 11, no time multiplexer is necessary to be used with second frequency driver 132 because the single frequency waveform can be transmitted constantly or without time variation. Meanwhile, if the reference transmitter 110 includes a tri-axial coil 112, then a first frequency waveform can be used for the x-axis coil 113, a second frequency waveform can be used for the y-axis coil 114, and a third frequency waveform can be used for the z-axis coil 115 so that the identity of the individual coils can be determined and maintained.

In any event, the components described above enable the execution of a method for determining the position of an invasive medical device 200 via the medical device position guidance system 100 of the present invention whereby at least one reference transmitter 110 is secured to a fixed anatomical landmark 60 of the subject 10, after which an electromagnetic field is generated using the at least one reference transmitter 110. Next, a receiver system 300 (e.g., a sensor 310 disposed within a distributed housing 500)

senses the electromagnetic field, and the location and orientation of each sensor 310, 312 of the receiver system 300 relative to the at least one reference transmitter is determined to create an anatomical coordinate system 101.

Further, at least one anatomical landmark 60 of the subject 10 in the reference transmitter coordinate system 102 is registered such that an in-scale anatomical coordinate system 101 of the subject 10's external anatomy 62 is created. Specifically, a pre-defined anthropometric relationship between the in-scale coordinate system 101 (see FIG. 3) of the subject 10's external anatomy 62 is used to determine the internal anatomical shape and size of the subject 10 and create an in-scale anatomical coordinate system 101 (see FIG. 12) representing the internal and external anatomy of the subject 10.

In doing so, an electromagnetic field is generated using an inserted transmitter 220, and the electromagnetic field of the inserted transmitter 220 is sensed using the sensors 310, 312 of the receiver system 300 such that the location and orientation of the sensors 310, 312 of the receiver system 300 can be determined relative to the inserted transmitter 220, after which the location and orientation of the in-scale anatomical coordinate system 101 can be plotted (see FIG. 12).

In another embodiment, the method can further include the steps of generating an electromagnetic field using an inserted transmitter 220; sensing the electromagnetic field of the inserted transmitter 220 using the receiver system 300; determining the location and orientation of each sensor 310, 312 of the receiver system 300 relative to the inserted transmitter 220; and plotting the location and orientation of the inserted transmitter 220 on the anatomical coordinate system 101.

In still another embodiment, each sensor 310, 312 of the receiver system 300 can be movable relative to the subject 10, wherein the method further comprises a step of periodically updating the location and orientation of each sensor 310, 312 of the receiver system 300 relative to the at least one reference transmitter 110. In some aspects, the periodic updating of the location and orientation of each sensor 310, 312 of the receiver system 300 relative to the at least one reference transmitter 110 can be continuous updating.

The method can also include the steps of providing a secondary transmitter 410 configured to provide additional information about the anatomy of the subject 10; and combining data from the secondary transmitter 410 about the anatomy of the subject 10 with the anatomical coordinate system 101 to create an anatomical map of the anatomy of the subject 10.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A medical device position guidance system comprising:
    at least one reference transmitter, wherein the at least one reference transmitter is configured to maintain a fixed position relative to a subject;
    a receiver system configured to receive signals from the at least one reference transmitter;
    a processor, wherein the at least one reference transmitter and the receiver system are operatively coupled to the processor; and
    a memory device storing instructions which when executed by the processor, cause the processor to:
        (i) receive signals relating to a location and orientation of the receiver system relative to the at least one reference transmitter; and
        (ii) using the received signals, create an anatomical coordinate system;
    wherein the memory device further includes information defining a pre-defined anthropometric relationship between the anatomical coordinate system of the subject's external anatomy and the internal anatomical shape and size of the subject.

2. The medical device position guidance system of claim 1, wherein the reference transmitter comprises a registration transmitter, wherein the registration transmitter is configured to be placed on an anatomical landmark of the subject, wherein the receiver system is configured to receive signals from the at least one registration transmitter;
    wherein the memory device stores instructions which when executed by the processor, cause the processor to:
        (i) receive signals relating to the location and orientation of the at least one registration transmitter relative to the receiver system;
        (ii) using the received signals relating to the location and orientation of the at least one transmitter relative to the receiver system, plot the location and orientation of the registration transmitter on the anatomical coordinate system; and
        (iii) register the anatomical landmark on the anatomical coordinate system such that the anatomical coordinate systems forms a representation of the subject's external anatomy.

3. The medical device position guidance system of claim 1, further comprising an inserted transmitter configured to be inserted into the subject, wherein the receiver system is configured to receive signals from the inserted transmitter;
    wherein the memory device stores instructions which when executed by the processor, cause the processor to:
        (i) receive signals relating to the location and orientation of the inserted transmitter relative to the receiver system; and
        (ii) using the received signals relating to the location and orientation of the inserted transmitter relative to the receiver system, plot the location and orientation of the inserted transmitter on the anatomical coordinate system.

4. The medical device position guidance system of claim 3, wherein the inserted transmitter is mounted to a catheter or mounted on a stylet configured to be inserted within a catheter.

5. The medical device position guidance system of claim 3, wherein the inserted transmitter comprises at least one coil configured to generate electromagnetic signals.

6. The medical device position guidance system of claim 5, wherein the at least one coil is a single-axis coil or a multi-axis coil.

7. The medical device position guidance system of claim 1, further comprising a display device operatively coupled to the processor;

wherein the memory device stores instructions which when executed by the processor, cause the processor to cause the display device to display the anatomical coordinate system.

8. The medical device position guidance system of claim 1, wherein each reference transmitter comprises a set of three coils oriented orthogonally to one another, wherein each of the coils is configured to transmit electromagnetic signals.

9. The medical device position guidance system of claim 1, wherein the receiver system includes a sensor comprising a tri-axial coil configured to receive electromagnetic signals.

10. The medical device position guidance system of claim 1, wherein the receiver system is configured to be able to move relative to the at least one reference transmitter.

11. The medical device position guidance system of claim 10, wherein the receiver system comprises at least two sensors configured to receive signals from the at least one reference transmitter.

12. The medical device position guidance system of claim 11 wherein each sensor of the receiver system comprises an independent housing such that each sensor of the receiver system is in a dynamic spatial relationship relative to each other.

13. The medical device position guidance system of claim 11, wherein the at least two sensors are enclosed in a unitary receiver housing.

* * * * *